(12) United States Patent
Fischer et al.

(10) Patent No.: US 12,419,892 B2
(45) Date of Patent: Sep. 23, 2025

(54) PHARMACEUTICAL COMPOSITIONS COMPRISING NILOTINIB

(71) Applicant: XSPRAY PHARMA AB, Solna (SE)

(72) Inventors: Andreas Fischer, Uppsala (SE); Thomas Andersson, Segeltorp (SE)

(73) Assignee: XSPRAY PHARMA AB, Solna (SE)

( * ) Notice: Subject to any disclaimer, the term of this patent is extended or adjusted under 35 U.S.C. 154(b) by 0 days.

(21) Appl. No.: 18/941,137

(22) Filed: Nov. 8, 2024

(65) Prior Publication Data

US 2025/0144096 A1     May 8, 2025

Related U.S. Application Data

(60) Provisional application No. 63/596,990, filed on Nov. 8, 2023.

(51) Int. Cl.
| | |
|---|---|
| *A61K 31/506* | (2006.01) |
| *A61K 9/14* | (2006.01) |
| *A61K 9/48* | (2006.01) |

(52) U.S. Cl.
CPC ............ *A61K 31/506* (2013.01); *A61K 9/146* (2013.01); *A61K 9/4816* (2013.01); *A61K 9/4858* (2013.01); *A61K 9/4866* (2013.01)

(58) Field of Classification Search
None
See application file for complete search history.

(56) References Cited

U.S. PATENT DOCUMENTS

| | | | |
|---|---|---|---|
| 8,163,904 | B2 | 4/2012 | Manley et al. |
| 10,314,830 | B2 | 6/2019 | Brisander et al. |
| 10,772,877 | B2 | 9/2020 | Brisander et al. |
| 10,874,671 | B2 | 12/2020 | Jain et al. |
| 11,376,243 | B2 | 7/2022 | Brisander et al. |
| 11,793,809 | B2 | 10/2023 | Jain et al. |
| 2015/0273070 | A1* | 10/2015 | Li .................... A61K 31/506 562/607 |
| 2020/0261449 | A1* | 8/2020 | Jain ................... A61K 9/1652 |
| 2024/0009188 | A1 | 1/2024 | Jain et al. |

FOREIGN PATENT DOCUMENTS

| | | |
|---|---|---|
| WO | 2013105894 A1 | 7/2013 |
| WO | 2013105895 A1 | 7/2013 |

OTHER PUBLICATIONS

Spray-Dried Dispersions—Particle Engineering of Spray Dried Dispersions: Considerations for Downstream Processing Goodwin et al. Drug Development & Delivery, 2017 (Year: 2017).*
Long-term outcomes with frontline nilotinib versus imatinib in newly diagnosed chronic myeloid leukemia in chronic phase: ENESTnd 10-year analysis Kantarjian et al. Leukemia (2021) 35:440-453 (Year: 2021).*
Buehler, G., History of Bioequivalence for Critical Dose Drugs, FDA, 2010 (70 pp.).
Guidance for Industry: Food-Effect Bioavailability and Fed Bioequivalence Studies, U.S. Department of Health and Human Services, Food and Drug Administration, Center for Drug Evaluation and Research (CDER), Dec. 2002 (12 pp.).
Guidance for Industry: M7(R1) Assessment and Control of DNA Reactive (Mutagenic) Impurities in Pharmaceuticals to Limit Potential Carcinogenic Risk, U.S. Department of Health and Human Services, Food and Drug Administration, Center for Drug Evaluation and Research (CDER), Dec. 2002 ("FDA's 2018 Guidance") (131 pp.).
Singamsetti et al., Forced Degradation Studies of Nilotinib Hydrochloride: Isolation, Identification, and Characterization of Impurities, International Journal of Pharmaceutical Sciences and Drug Research 2020;12(5):537-543.
USP 32, General Notices and Requirements, 2009 (pp. 1-12).
Puppala et al., Trace level detection and quantification of genotoxic impurities 3-amino-4-methylbenzoate, 3-amino-4-methylbenzoic acid, and 3-(4-methyl-1H-imidazol-1-yl)-5(trifluoromethyl) aniline in Nilotinib dihydrochloride active pharmaceutical ingredient using liquid chromatography-tandem mass spectrometry, Sep. Sci. Plus (2022) 5:349-356.
Tasigna® (nilotinib) capsules, prescribing information, as of Sep. 23, 2021 (39 pp.).
Nilotinib Hydrochloride Monohydrate monograph from the European Pharmacopoeia, Tenth Edition, vol. I (2019), 5 pp.
Tasigna Chemistry Review(s) for NDA 22-068 (2007) 23 pp.
Meloun et al., A Search for the Protonation Model with Thermodynamic Dissociation Constants and (Extra) Thermodynamics of Nilotinib Hydrochloride (Tasigna), Journal of Solution Chemistry (2019) 48:702-731.
The Handbook of Pharmaceutical Excipients, 6th Edition, Rowe et al. (2009), pp. 43-46, 181-183, 197-198, 326-395, 355-356, 506-509, 517-522, 525-533, 581-585, 764-765, and 766-770.
Chemical Abstract Service No. 25212-88-8 (2025) 2 pp.
Chemical Abstract Service No. 641571-10-0 (2025) 2 pp.
Remington: The Science and Practice of Pharmacy, 21st Edition (2006), pp. 212 and 235-245.
Vehring, R., Pharmaceutical particle engineering via spray drying, Pharm. Res. (2007) 25(5): 999-1022.
Jesson et al., Carbon dioxide-mediated generation of hybrid nanoparticles for improved bioavailability of protein kinase inhibitors, Pharm. Res. (2014) 31(3): 694-705.

* cited by examiner

*Primary Examiner* — Jeffrey S Lundgren
*Assistant Examiner* — Eric Tran
(74) *Attorney, Agent, or Firm* — Merchant & Gould P.C.; Daniel R. Evans

(57) ABSTRACT

Disclosed herein is a composition comprising: an amorphous solid dispersion (ASD) comprising nilotinib and at least one polymeric stabilizing and matrix-forming component; and at least one solid organic acid in admixture with the ASD, and uses thereof in the treatment of proliferative disorder.

20 Claims, No Drawings

PHARMACEUTICAL COMPOSITIONS COMPRISING NILOTINIB

RELATED APPLICATION

This application claims priority to U.S. Provisional Patent Application No. 63/596,990, filed on Nov. 8, 2023, which is incorporated by reference.

FIELD

Disclosed herein is a composition comprising: an amorphous solid dispersion (ASD) comprising nilotinib and at least one polymeric stabilizing and matrix-forming component; and at least one solid organic acid in admixture with the ASD, as well as uses thereof in the treatment of proliferative disorders.

BACKGROUND

Protein kinase inhibitors (PKIs) have been studied for their potential use in treating various disorders of cellular proliferation, including cancer. The potential for PKIs as a treatment is based on the role that protein kinases are known to play in regulating many cellular pathways, including those involved in signal transduction. Dysregulation of protein kinases has been implicated in the development and progression of many cancers, which suggests that PKIs may be useful as a treatment for disorders or diseases such as cancer that are caused by uncontrolled overexpression or upregulation of protein kinases.

One such PKI is nilotinib, which is currently marketed as an immediate-release capsule formulation for oral administration under the brand name Tasigna®. Tasigna® contains crystalline nilotinib monohydrochloride monohydrate and is available in three capsule unit dosage forms corresponding to 50 mg, 150 mg, and 200 mg equivalent nilotinib free base. Tasigna® was first approved by U.S. Food and Drug Administration (FDA) in 2007 and is indicated for the treatment of (as of 2023):

Adult and pediatric patients greater than or equal to 1 year of age with newly diagnosed Philadelphia chromosome positive chronic myeloid leukemia (Ph+CML) in chronic phase.

Adult patients with chronic phase (CP) and accelerated phase (AP) Ph+CML resistant to or intolerant to prior therapy that included imatinib.

Pediatric patients greater than or equal to 1 year of age with Ph+CML-CP and CML-AP resistant or intolerant to prior tyrosine-kinase inhibitor (TKI) therapy.

The recommended adult dose is 300 mg (consisting of two 150 mg capsules) orally twice daily for newly diagnosed Ph+CML-CP and 400 mg (consisting of two 200 mg capsules) orally twice daily for resistant or intolerant Ph+CML-CP and CML-AP. The current prescribing information for Tasigna® instructs the patient to dose Tasigna® twice daily on an empty stomach and avoid food 2 hours before and 1 hour after taking a dose. Tasigna® is accompanied by a food effect and the requirement to take Tasigna® twice-a-day without food (for a three-hour period for each dose) is a considerable burden to patients. Further, poor adherence to the dosing recommendations can be very detrimental to patients.

Tasigna® is contraindicated in patients with hypokalemia, hypomagnesemia, or long QT syndrome. Prolongation of the QT interval can predispose to a potentially fatal polymorphic ventricular tachycardia called torsades de pointes (TdP). Although usually self-limited, TdP may degenerate into ventricular fibrillation and cause sudden death. The Tasigna® prescribing information thus contains a boxed warning of QT prolongation and sudden death.

This effect on the QT interval is likely due to the increase in exposure (expressed as area-under-the-curve, or AUC) and/or maximum plasma concentration (Cmax) that can occur when Tasigna® is taken with food. For example, a single 400-mg dose of Tasigna® taken 30 minutes after a high-fat meal, increased AUC and Cmax by 82% and 112%, respectively, as compared to levels obtained under fasting conditions. Such an increase in serum levels may also exacerbate or increase the prevalence of common side effects such as nausea, diarrhea, rash, headache, muscle and joint pain, tiredness, vomiting, and fever; as well as more serious side effects such as low blood cell counts, decreased blood flow to the heart or brain, pancreas inflammation, liver problems, and bleeding problems.

The Tasigna® prescribing information also contains a drug interaction with proton pump inhibitors (PPIs). Concomitant use with a proton pump inhibitor (PPI) decreased nilotinib concentrations compared to Tasigna® alone, which may reduce Tasigna® efficacy. Patients are thus recommended to avoid concomitant use of PPI. As an alternative to PPIs, patients are recommended to use H2 blockers approximately 10 hours before or approximately 2 hours after the dose of Tasigna®, or use antacids approximately 2 hours before or approximately 2 hours after the dose of Tasigna®.

Nilotinib impurity A, 3-(4-methylimidazol-1-yl)-5-(trifluoromethyl) aniline (CAS No. 641571-11-1), is classified as a potentially genotoxic or mutagenic compound, see for example discussion in Li ([0117]), Singamsetti and Puppala, 350. (Internal evaluations (not disclosed herein) suggest that Nilotinib impurity A may not be genotoxic.) Regardless, classifying a compound as potentially genotoxic or mutagenic is concerning, as it suggests the compound may pose a health risk and should thus be limited in products for human use. Regulatory agencies, such as the FDA and the European Medicines Agency (EMA), have specific guidelines and regulations for assessing and managing the risks associated with genotoxic compounds, particularly in the context of pharmaceuticals and chemical safety.

Nilotinib impurity A is a synthesis related impurity (one of the starting materials for the synthesis of nilotinib) and a degradation related impurity. It is formed from nilotinib under acidic and alkaline (basic) hydrolysis conditions. Singamsetti.

There is thus an unmet medical need for a stable nilotinib pharmaceutical composition, which does not generate significant amounts of nilotinib impurity A overtime and under various storage conditions.

Drug companies can submit an abbreviated new drug application (ANDA) to U.S. Food and Drug Administration (FDA) for approval to market a generic drug that is the same as (or bioequivalent to) the brand-name product. Likewise, drug companies can submit a 505(b)(2) application to the FDA for approval to market an alternative drug that is bioequivalent to the brand-name product. With some differences, the review process for the ANDA and 505(b)(2) application is comparable. The FDA's Office of Generic Drugs reviews the application to make certain drug companies have demonstrated that the generic medicine can be substituted for the brand-name medicine.

An important consideration for approval of the generic or improved drug is showing bioequivalence to the reference listed drug. The FDA defines bioequivalence as the absence of a significant difference in the rate and extent to which the active ingredient becomes available when administered at the same molar dose under similar conditions in an appropriately designed study. See, e.g., Buehler 2010.

In order to determine bioequivalence, a randomized, crossover trial is conducted with both the generic drug being assessed and the brand-name drug as the control. In these studies, a number of pharmacokinetic (PK) parameters are assessed, including maximum plasma concentration of a drug (Cmax) and drug plasma exposure over time (or area under the curve, (AUC)).

These parameters help assess how the rate and extent of the availability of the generic drug compares to the control. As the FDA requires, there must be no significant difference in the rate and extent to be deemed bioequivalent.

According to current regulatory (viz., FDA and European Medicines Agency) guidance documents, bioequivalence can be declared when the 90% confidence interval (CI) for the ratio of mean values for Cmax and AUC for generic drug vs. original drug falls within the interval 80-125%, as evaluated in a randomized, cross-over trial.

There is thus a high medical need and high commercial incentives for companies to develop a drug that is considered a generic drug according to the relevant national regulatory standards. Such regulatory standards are high and difficult to meet since safety and efficacy is a major concern for all regulatory authorities. It is thus a major challenge to develop a drug that is considered fully bioequivalent and substitutable for the reference listed drug (RLD).

There is notable interindividual heterogeneity in drug response, affecting both drug efficacy and toxicity, resulting in patient harm and the inefficient utilization of limited healthcare resources. It has been reported that the proportion of patients who respond beneficially to the first drug offered in the treatment of a wide range of diseases is typically just 50-75%. Drug absorption is an important component of drug response where interindividual variability leads to patient harm and the excessive and inefficient use of limited healthcare resources.

There is thus an unmet need for a pharmaceutical composition that is bioequivalent to Tasigna® (nilotinib monohydrochloride monohydrate), but with fewer drawbacks like inter- or interindividual variation, food interaction, bioavailability dependent of gastric transit time and the like.

A drug interaction is a change in the action or side effects of a drug caused by concomitant administration with a food, beverage, supplement, or another drug. The majority of clinically relevant food-drug interactions are caused by food-induced changes in the bioavailability of the drug. Since the extent of a food effect on oral bioavailability strongly depends on the type and composition of the food as well as on the dietary protocol during the study, the FDA issued a guidance in 2002 for conducting bioavailability and bioequivalence studies under fed conditions (GFI, Food Effect). See FDA's 2002 Guidance. This so-called FDA standard meal meanwhile represents the general standard for food effect studies and therefore, the majority of pharmacokinetic data on food effects that were published are based on this particular meal. The final evaluation of the food effect is based on the 90% confidence intervals of the ratios of AUC and Cmax obtained following drug administration under fasted and fed conditions. According to the ratio of the AUC determined after fasting and after fed drug administration, positive (increased oral bioavailability) and negative (reduced oral bioavailability) food effects are distinguished.

As generally interpreted, "food effect" broadly refers to all aspects of interactions of food on drug dissolution, absorption, distribution, metabolism and elimination. The implications of food effect include changes in bioavailability, rate of on-set, duration of therapeutic effect and incidence and seriousness of side effects. The magnitude of a food effect is generally greatest when the drug product is administered shortly after a meal is ingested.

In practice, a food effect is generally assessed by measuring standard pharmacokinetic parameters observed upon administration of a drug product to a subject in a fasted state, versus the same measurements observed upon administration to the same subject in a fed state. Relevant pharmacokinetic parameters can include AUC, Cmax, and/or Tmax. AUC can be assessed for a specified time interval (such as AUC(0-12 h) or AUC(0-24 h), for example), or as AUC(0-last) or AUC(0-∞). Typically, data for a number of test subjects is pooled for analysis. For further information about food effect studies, refer to the FDA's 2002 Guidance.

As used in relation to the methods of the present disclosure the phrase "food effect" refers to a relative difference in one or more of AUC, Cmax, and/or Tmax for an active substance, when said substance or a composition thereof (such as a solid dispersion or pharmaceutical composition) is administered orally to a human subject, concomitantly with food or in a fed state, as compared to the measured value for the same parameter when the same amount of active substance in a formulation is administered to the same subject in a fasted state.

The food effect F is calculated as $$F=(Yfed-Yfasted)/Yfasted$$

wherein Yfed and Yfasted are the measured values of AUC, Cmax or Tmax in the fed and fasted state, respectively.

The phrase "positive food effect" refers to a food effect where the AUC and/or Cmax is higher when the drug product is administered orally in a fed state than when it is administered in a fasted state. The phrase "negative food effect" refers to a food effect where the AUC and/or Cmax is lower when the drug product is administered orally in the fed state than when it is administered in the fasted state.

In assessing food effect, data obtained from fasted and fed studies is processed using conventional pharmacokinetic statistical analyses and methods. Fasted and fed studies may be single-dose studies or steady-state studies, as appropriate. Using pooled data from a suitable number of subjects, an absence of food effect is indicated when the 90% CI for the ratio of population geometric means between fed and fasted administrations, based on log-transformed data, is contained in the equivalence limits of 80% to 125% for AUC(0-∞) (or AUC(0-t), e.g., AUC(0-24 h), when appropriate) and Cmax. On the other hand, an absence of food effect is not established if the 90 percent CI for the ratio of population geometric means between fed and fasted administrations, based on log-transformed data, is not contained in the equivalence limits of 80% to 125% for either AUC(0-∞) (or AUC(0-t), e.g., AUC(0-24 h), when appropriate) or Cmax.

In the methods of the present disclosure, "without a food effect" means that the relative difference is not substantially large, e.g., less than 20%, or less than 15%, or less than 10%, for AUC (which can be, for example, AUC(0-24 h), AUC (0-last) or AUC(0-∞)) and/or Cmax, for nilotinib when the ASD or pharmaceutical composition of the present disclosure is administered orally, concomitantly with food or in a fed state, as compared to the measured value for the same parameter when the same ASD or pharmaceutical composition is administered in a fasted state. (As used herein, for a relative difference stated as a percentage, each stated range is with respect to the absolute value of that relative difference, i.e., "less than 20%" means that the relative difference F falls in the range −20%<F<+20%.)

In the methods of the present disclosure, "without regard to consumption of food" means that no consideration has to be made whether the ASD or pharmaceutical composition of the present disclosure is being administered to the subject or patient concomitantly with food, or whether the patient or subject is in a fed state or fasted state. The administration will be expected to provide a therapeutically relevant exposure and will not be expected to cause an unsafe overexposure, regardless of whether the patient or subject is in a fed state or fasted state.

Concomitant use of antacid preparations including proton pump inhibitor (PPIs) with other medications is common. The potential for antacid-drug interactions is dependent upon the chemistry and physical properties of the antacid preparation and might be increased if the API has a pH-dependent solubility. These pH-dependent solubility differences might lead to pH-dependent dissolution profiles. Many APIs, like nilotinib, are known to have a pH-dependent solubility. However, the physical form of the API and/or the pharmaceutical excipients used in the final drug product, may decrease or even diminish the pH-dependent solubility of the API. It is advantageous if the final drug product shows a small, or non-existing, pH-dependent dissolution profile.

SUMMARY

An aspect of the present disclosure relates to an amorphous solid dispersion ("ASD") comprising nilotinib and at least one polymeric stabilizing and matrix-forming component. Another aspect of the present disclosure relates to a composition comprising: an ASD comprising nilotinib and at least one polymeric stabilizing and matrix-forming component; and at least one solid organic acid. In some embodiments, the composition comprising: an ASD comprising nilotinib and at least one polymeric stabilizing and matrix-forming component in admixture with at least one solid organic acid.

The composition comprising an ASD comprising nilotinib and at least one polymeric stabilizing and matrix-forming component in admixture with at least one solid organic acid has an improved dissolution.

In another aspect, the present disclosure provides stable pharmaceutical compositions comprising the ASDs disclosed herein.

Pharmaceutical stability refers to the ability of a pharmaceutical product to maintain its physical, chemical, and therapeutic properties over time and under various storage conditions. This is a critical aspect of pharmaceutical development, production, and quality control to ensure that drugs remain safe and effective for their intended use throughout their shelf life. Pharmaceutical stability encompasses several key aspects, such as:

Chemical Stability: This aspect of stability assesses whether the active pharmaceutical ingredient (API) and other components of the drug product undergo chemical changes over time. It aims to ensure that the drug remains free from degradation products that could be harmful or reduce its effectiveness.

Physical Stability: Physical stability focuses on changes in the physical properties of the drug product, including color, odor, taste, texture, and appearance. For example, pharmaceuticals should not undergo changes such as crystallization, clumping, or separation.

Therapeutic Stability: Therapeutic stability examines whether the drug maintains its intended therapeutic effect over time. This includes assessing the drug's potency and efficacy.

Container and Closure Integrity: The packaging of pharmaceutical products plays a crucial role in stability. Container and closure systems should prevent exposure to moisture, oxygen, light, and contaminants that could affect the product's stability.

Stress Testing: Stress testing involves subjecting the drug product to various environmental conditions, such as high temperature and humidity, to accelerate stability testing and assess potential degradation products.

Stability testing is a mandatory part of the drug development process, and regulatory agencies, like the FDA and the EMA, provide guidelines for conducting stability studies. The goal is to establish the product's shelf life (expiration date) and storage recommendations, ensuring that consumers receive safe and effective pharmaceuticals.

In certain aspects, the term "stable" refers to chemical stability, wherein not more than 2% w/w of total related substances are formed on storage at accelerated conditions of stability at 40° C. and 75% relative humidity or at 25° C. and either 60% or 75% relative humidity for a period of at least three months or to the extent necessary for use of the composition.

In other certain aspects, the term "stable" refers to chemical stability, wherein specific related substances (e.g. degradation products, including Nilotinib Impurity A) may not be formed and present in the composition at levels exceeding its specified limit upon storage at accelerated conditions at 40° C. and either 60% or 75% relative humidity or at 25° C. and 60% relative humidity for a period of at least three months or to the extent necessary for use of the composition.

For genotoxic impurities in pharmaceutical compositions the specified levels which may not be exceeded is often in the range of 1 to 100 ppm (0.0001 to 0.01% w/w). The permitted genotoxic impurity levels depend on the specific substance and dose, and length of treatment, and can be established by the guidance given in guideline documents provided by regulatory authorities. See, e.g., FDA's 2018 Guidance.

Accordingly, an aspect disclosed herein relates to a composition (or a pharmaceutical composition) comprising: an ASD comprising nilotinib and at least one polymeric stabilizing and matrix-forming component; and ascorbic acid in admixture with the ASD having about 0.1 to about 100 ppm of Nilotinib Impurity A.

Yet another aspect of the present disclosure relates to nilotinib amorphous solid dispersions (ASDs), pharmaceutical compositions of nilotinib ASDs, and methods of use comprising administration of the pharmaceutical compositions of nilotinib ASDs. The nilotinib ASDs and the pharmaceutical compositions of the present disclosure may provide particular advantages over conventional crystalline nilotinib formulations, such as Tasigna® (nilotinib monohydrochloride monohydrate).

Moreover, certain ASDs and pharmaceutical compositions of the present disclosure unexpectedly provide a pharmacokinetic profile similar to that of Tasigna®, even when the dose of nilotinib administered by the pharmaceutical compositions is a fraction (e.g., from about 0.20 to about 0.80) of the dose of nilotinib normally administered when using Tasigna®. Therefore, the disclosure provides pharmaceutical compositions that can be administered at a lower dose than Tasigna®, but that would be expected to provide a comparable therapeutic effect.

As another advantage, pharmaceutical compositions of the disclosure may achieve a reduced inter-subject and/or intra-subject variability, as compared to the variability observed for Tasigna®.

Thus, the ASDs and the pharmaceutical compositions of the present disclosure may offer a safer but equally effective presentation of nilotinib as compared to the currently available product, i.e., Tasigna® (crystalline nilotinib monohydrochloride monohydrate).

Yet another aspect of the present disclosure relates to a method of treating a disease which responds to an inhibition of protein kinase activity, such as a proliferative disorder. In some embodiments, the method comprises administration of an ASD or pharmaceutical composition disclosed herein to a patient. In some embodiments, the composition is administered without regard to consumption of food. In some embodiments, the composition is administered without regard to whether the patient is in a fasted state or a fed state.

As another advantage, pharmaceutical compositions of the disclosure may achieve a reduced inter-subject and/or intra-subject variability, as compared to the variability observed for Tasigna®.

DETAILED DESCRIPTION

The present disclosure relates to nilotinib ASDs, compositions comprising nilotinib ASDs, pharmaceutical compositions comprising nilotinib ASDs, and methods of use comprising administration of nilotinib ASDs or the pharmaceutical compositions. The nilotinib ASDs and the pharmaceutical compositions of the present disclosure may provide advantages over conventional immediate-release nilotinib capsule formulations, such as Tasigna® including crystalline nilotinib monohydrochloride monohydrate.

Amorphous Solid Dispersions of Nilotinib

An aspect of the present disclosure relates to an amorphous solid dispersion ("ASD") comprising nilotinib and at least one polymeric stabilizing and matrix-forming component.

The present disclosure (and appended claims) includes the expression "a" or "an," which absent information to the contrary is equivalent to "at least one" or "one or more."

In some embodiments, the ASD comprises nilotinib and at least one polymeric stabilizing and matrix-forming component.

In the ASDs of the disclosure, the nilotinib may be as a free base and may be anhydrous, a hydrate or a solvate.

In the description of the ASDs and pharmaceutical compositions below, and in the claims, any reference to "nilotinib" refers broadly to nilotinib free base, salts of nilotinib (e.g., hydrochloride salt of nilotinib), anhydrous nilotinib (or salts thereof), hydrates or solvates of nilotinib, and hydrates or solvates of nilotinib salts as suitable alternatives, unless specified.

Examples of suitable "polymeric stabilizing and matrix-forming component" includes, but is not limited to, methyl cellulose, hydroxyethyl cellulose, hydroxypropyl cellulose, hydroxypropyl methylcellulose (HPMC, e.g. Methocel E3, E15 and K100LV and Pharmacoat), hydroxypropyl methylcellulose acetate succinate (HPMC AS), hydroxypropyl methylcellulose phthalate (e.g. HPMCP-HP55), polyvinylpyrrolidone (e.g. PVP 30K and PVP 90K), polyvinyl acetate phthalate (PVAP), copovidone (aka, copolyvidone (e.g. Kollidon VA 64)), crospovidon (e.g. Kollidon CL), polyvinyl alcohol (PVA), methacrylic acid and ethylacrylate copolymer (e.g. Kollicoat ME), methacrylate acid and methyl methacrylate copolymer (e.g. Eudragit L100-55), polyethylene glycol (PEG), DL lactide/glycolide copolymer, poly DL-lactide, cellulose acetate phthalate (CAP), aminoalkyl methacrylate copolymers (e.g. Eudragit RL100, RL PO or RS PO), carbomer homopolymer Type A (e.g. Carbopol 971P), carbomer homopolymer Type B (e.g. Carbopol 974P) and Poloxamers (e.g. Pluronics, Kolliphor).

Yet another aspect relates to a particulate ASD comprising nilotinib and at least one polymeric stabilizing and matrix-forming component, where the particulate ASD has a bulk density of about 0.46 g/mL.

Yet another aspect relates to a particulate ASD comprising nilotinib and at least one polymeric stabilizing and matrix-forming component, where the particulate ASD has a tapped density of about 0.63 g/mL.

Yet another aspect relates to a particulate ASD comprising nilotinib and at least one polymeric stabilizing and matrix-forming component, where the particulate ASD has a particle size distribution of about 72% w/w (<125 µm), about 20.8% w/w (125-250 µm), about 5.7% w/w (250-425 µm), about 0.7% w/w (425-600 µm), and about 0.8% w/w (>600 µm).

Methods of Making ASDs and Particulate ASDs

The nilotinib ASDs of the present disclosure may be prepared by a variety of known methods. ASD manufacturing methods can be broadly classified into solvent-based methods and melting or fusion methods. Solvent evaporation-based methods include spray drying (SD), electrospraying, freeze drying, drum drying and rotary evaporation, wherein the drug and polymer are dissolved in a solvent which is then evaporated to form an ASD.

In one aspect of the present disclosure the nilotinib ASDs are prepared as described in e.g., WO 2013/105894 and WO 2013/105895. As an example, ASDs are prepared by subjecting to the system described herein two fluid streams where one fluid stream comprises a solution comprising at least one solvent, nilotinib, and the at least one polymeric stabilizing and matrix-forming component ("PSMFC") (about 2-10% w/v), where the ratio of nilotinib-to-PSMFC is about 10-90% w/w and where another fluid stream comprises an antisolvent. The present disclosure (and appended claims) includes the expression "about," which is understood to mean approximately, which according to the USP 32, 8.2 indicates a quantity within 10%. It will be understood that "about" refers to the experimental variation in a recited value, which in certain cases, "about" may refer to a lower degree of experimental variation, such as +5%, +2%, +1%, etc. One will appreciate that the absence of the qualifying expression "about" associated with a recited value does not mean that the recited value is without experimental variation.

An important characteristic of the system disclosed therein is that the two fluid streams should merge within a nozzle at an angle in the interval of from about 45° to about 135°, e.g., about 90°, and sprayed into a particle formation/separation function. In principle, the system allows for producing particles of predetermined size and/or morphology for example nilotinib as the active pharmaceutical ingredient and $CO_2$ as a fluid antisolvent under supercritical or subcritical conditions. The solid dispersion particles are dried by flushing $CO_2$ through the retained particles in order to extract any remaining solvent. The precipitation vessel is then depressurized and the particles can be collected.

Illustrative fluids which can be used as an antisolvent are (a) gaseous at room temperature and atmospheric pressures ("group (a) fluid"), or (b) liquid at room temperature and atmospheric pressure ("group (b) fluid").

The antisolvent is typically selected for its ability to be readily dispersed into small droplets and for its ability to act as an atomizing agent and antisolvent against the nilotinib present in the solution.

Fluids according to group (a) may be selected from carbon dioxide (Pc=74 bar and Tc=31° C.) (preferred), nitrous oxide (Pc=72 bar and Tc=36° C.), sulphur hexafluoride (Pc=37 bar and Tc=45° C.), ethane (Pc=48 bar and Tc=32° C.), ethylene (Pc=51 bar and Tc=10° C.), xenon (Pc=58 bar and Tc=16° C.), trifluoromethane (Pc=47 bar and Tc=26° C.), chlorotrifluoromethane (Pc=39 bar and Tc=29° C.) and nitrogen (Pc=34 bar and Tc=−147° C.) and mixtures containing these compounds/elements. Pc stands for critical pressure and Tc for critical temperature.

Fluids according to group (b) are typically selected among conventional liquids of the same general types as discussed for solvents above but with the difference that the nilotinib present in the solution must be poorly soluble in the antisolvent. Particular liquids of group (b) comprise methanol, ethanol, acetone/water and mixtures containing one or more of these fluids.

The fluid antisolvents of group (a) above are typically used at pressures and temperatures providing i) supercritical conditions (supercritical fluid) or ii) subcritical conditions (subcritical fluid) in the particle formation function and/or upstream of this function, such as in the mixing function and upstream of this latter function.

With reference to the preceding paragraph, variant (i) means pressures and temperatures which are typically above the critical pressure Pc and critical temperature Tc of the antisolvent used. For the pressure this typically means pressures in the interval (1.0-7.0)×Pc or in the interval ≥10 bar, suitably ≥20 bar with preference for ≥30 bar, higher than Pc with illustrative upper limits being 100 bar, 200 bar and 300 bar higher than Pc. For the temperature this typically means temperatures within (1.0-4.0)×Tc or in the interval of ≥5° C., suitably ≥10° C. with preference for ≥15° C. above Tc with illustrative upper limits being 10° C., 40° C. and 50° C. above Tc.

Variant (ii) means that at least one of temperature and pressure, with preference for only the temperature, is/are below the critical value; Tc and Pc, respectively. Thus, the temperature may be in the interval of (0.1-1)×Tc, such as (0.5-1)×Tc, or lower. Further, the temperature may be low, such as −10° C. or −30° C. These temperatures may be combined with pressures as defined in the preceding paragraph or with pressures lower than the Pc of the used antisolvent. For carbon dioxide this means that the temperature in the particle formation function is <+31° C., such as about +25° C. or lower combined with a pressure above or below 74 bar.

The antisolvents of group (b) above are typically used in the subcritical state, i.e. as a subcritical fluid.

A suitable solvent is an organic solvent selected from the group consisting of DMSO, trifluoroethanol, acetone, tetrahydrofuran, ethyl acetate, dimethylacetamide, or a mixture thereof.

In one aspect, the amount of nilotinib in an ASD comprising nilotinib and at least one PSMFC ranges from about 10% by weight of the ASD to about 90% by weight of the ASD, and all values in between, such as about 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, and 85% w/w. One may appreciate that the amount of nilotinib in the ASD may be, for example, about 10% by weight to about 40% by weight, about 20% by weight to about 40% by weight, about 20% by weight to about 30% by weight, and about 25% by weight; or about 30% by weight to about 50% by weight, or about 35% by weight to about 40% by weight. One also may appreciate that the ASD may further comprise one or more pharmaceutically acceptable excipients disclosed herein, including, for example, an antioxidant.

The ASD may be milled to obtain a particulate ASD by any suitable milling method, such as hammer milling, impact milling, ball milling, and the like.

For instance, milling may be performed by feeding the ASD comprising nilotinib and at least one PSMFC to a suitable mill (e.g., a Fitzmill (Model DAs06) with the impact blades in a knife forward position) with a milling speed of, for example, about 4700 rpm, and with a collection container including sieves having mesh sizes of 30, 40, 60, and 120, where particles having <125 μm being collected in the bottom of the pan.

The milled ASD (aka "particulate ASD") has one or more of the following features: (1) a bulk density of about 0.42 g/mL, (2) a tapped density of about 0.63 g/mL, and (3) a particle size distribution of about 72% w/w (<125 μm), about 20.8% w/w (125-250 μm), about 5.7% w/w (250-425 μm), about 0.7% w/w (425-600 μm), and about 0.8% w/w (>600 μm).

Compositions

Another aspect of the present disclosure relates to a composition comprising: an ASD comprising nilotinib and at least one polymeric stabilizing and matrix-forming component; and at least one solid organic acid in admixture with the ASD. The expression "admixture" refers mixing the at least one solid organic acid with particles comprising the nilotinib-containing ASD, where the mixing includes any suitable mixing step, such as powder mixing, blending, granulation, co-dissolving, co-precipitation, co-milling, co-screening, and the like. The ASD may also be particulate ASD.

One will appreciate that the expression "comprising" may be replaced with the expression "consisting of," such that the above-mentioned aspect relates to a composition consisting of: an amorphous solid dispersion (ASD) comprising nilotinib and at least one polymeric stabilizing and matrix-forming component; and at least one solid organic acid in admixture with the ASD.

The at least one solid organic acid is selected from the group consisting of 2-hydroxyethanesulfonic acid, 4-aminosalicylic acid, adamantanecarboxylic acid, adipic acid, ascorbic acid, aspartic acid, azelaic acid, benzenesulfonic acid, benzoic acid, cinnamic acid, citric acid, cyclohexanecarboxylic acid, decanoic acid, dodecanoic acid, ethane-1,2-disulfonic acid, ethane-sulfonic acid, fumaric acid, glutamic acid, glycolic acid, hydroxymaleic acid, maleic acid, malic acid, mandelic acid, methylmaleic acid, octanoic acid, oxalic acid, phenylacetic acid, phthalic acid, pimelic acid, salicylic acid, suberic acid, succinic acid, and tartaric acid.

Yet another aspect of the present disclosure relates to a composition comprising: an ASD comprising nilotinib and at least one polymeric stabilizing and matrix-forming component; and ascorbic acid in admixture with the ASD.

And yet another aspect relates to a composition consisting of: an ASD comprising nilotinib and at least one polymeric stabilizing and matrix-forming component; and ascorbic acid in admixture with the ASD.

Ascorbic acid is a water-soluble substance found in citrus and other fruits and vegetables, and is also sold as a dietary supplement, as vitamin C. Ascorbic acid exists as two enantiomers commonly denoted "l" (for "levo") and "d" (for "dextro") of which the I-isomer is the naturally occurring one. Ascorbic acid is an essential nutrient involved in the repair of tissue, the formation of collagen, and the enzymatic production of certain neurotransmitters. It is required for the functioning of several enzymes and is important for immune system function and is also used to prevent and treat scurvy.

Ascorbic acid is a weak acid and has a pKa of about 4.2.

A suitable amount of ascorbic acid is about 0.1-10 times the amount of nilotinib (weight to weight), such as 0.5-5, 0.8-4, 1-3, 1.2-2.5, 1.3-2, 1.3-1.6, 1.4-1.5, or 1.4-1.7. An unexpected finding disclosed herein relates to the observation that a composition comprising a nilotinib-containing ASD in admixture with ascorbic acid resulted in substantially lower amounts of Nilotinib impurity A after storage at 40° C. and either 60% or 75% relative humidity.

In one aspect, the ascorbic acid comprises/-ascorbic acid, d-ascorbic acid, or a combination thereof. d-ascorbic acid is alternatively referred to as erythorbic acid. In yet another aspect, the ascorbic acid comprises/-ascorbic acid.

A further aspect of the present disclosure relates to a composition comprising: an ASD comprising nilotinib and at least one polymeric stabilizing and matrix-forming component; and ascorbic acid in admixture with the ASD having about 0.1 to about 100 ppm of Nilotinib Impurity A and all values in between including 0.5 ppm, 1 ppm, 2 ppm, 3 ppm, 4 ppm, 5 ppm, 6 ppm, 7 ppm, 8 ppm, 9 ppm, 10 ppm, 20 ppm, 30 ppm, 40 ppm, 50 ppm, 60 ppm, 70 ppm, 80 ppm, and 90 ppm.

And yet a further aspect relates to a composition consisting of: an ASD comprising nilotinib and at least one polymeric stabilizing and matrix-forming component; and ascorbic acid in admixture with the ASD having about 0.1 to about 100 ppm of Nilotinib Impurity A and all values in between.

Pharmaceutical Compositions

An aspect of the present disclosure relates to a pharmaceutical composition comprising: an ASD comprising nilotinib and at least one polymeric stabilizing and matrix-forming component; at least one solid organic acid in admixture with the ASD; and one or more pharmaceutically acceptable excipients. The ASD may also be particulate ASD.

An alternative aspect relates to a pharmaceutical composition consisting of: an ASD comprising nilotinib and at least one polymeric stabilizing and matrix-forming component; at least one solid organic acid in admixture with the ASD; and one or more pharmaceutically acceptable excipients.

Another aspect of the present disclosure relates to a pharmaceutical composition comprising: an ASD comprising nilotinib and at least one polymeric stabilizing and matrix-forming component; ascorbic acid in admixture with the ASD; and one or more pharmaceutically acceptable excipients.

Another alternative aspect relates to a pharmaceutical composition consisting of: an ASD comprising nilotinib and at least one polymeric stabilizing and matrix-forming component; ascorbic acid in admixture with the ASD; and one or more pharmaceutically acceptable excipients.

In yet another aspect, the pharmaceutical composition comprises: an ASD comprising nilotinib and at least one polymeric stabilizing and matrix-forming component; ascorbic acid and citric acid in admixture with the ASD.

In yet another alternative aspect, the pharmaceutical composition consists of: an ASD comprising nilotinib and at least one polymeric stabilizing and matrix-forming component; ascorbic acid and citric acid in admixture with the ASD.

As with the composition disclosed herein, a suitable amount of ascorbic acid is about 0.1-10 times the amount of nilotinib (weight to weight), such as 0.5-5, 0.8-4, 1-3, 1.2-2.5, 1.3-2, 1.3-1.6, 1.4-1.5, or 1.4-1.7.

The pharmaceutical compositions of the present disclosure may be in a dosage form appropriate for oral administration. In some embodiments, the pharmaceutical compositions may be in the form of granules or may be prepared as granules as an intermediate step to forming another oral dosage form, such as capsules, tablets, sprinkles, or pellets. In some embodiments, the pharmaceutical compositions may be in a solid dosage form for oral administration, such as a capsule, tablet, sprinkle, or pellet. The pharmaceutical composition may also be in the form of an aqueous or nonaqueous suspension or solution. Such compositions may be prepared using known excipients and known preparation methods.

Pharmaceutical Excipients

A pharmaceutical excipient is a substance formulated alongside the active ingredient of a medication, included for example for the purpose of long-term stabilization, bulking up solid pharmaceutical compositions that contain potent active ingredients in small amounts (thus often referred to as "bulking agents", "fillers", or "diluents"), or to confer a therapeutic enhancement on the active ingredient in the final dosage form, such as facilitating drug absorption, reducing viscosity, or enhancing solubility. A pharmaceutical excipient can also be useful in the manufacturing process, to aid in the handling of the active substance concerned such as by facilitating powder flowability or non-stick properties, in addition to aiding in vitro stability such as prevention of denaturation or aggregation over the expected shelf life.

Fillers/Binders

Many pharmaceutical excipients have dual functionality and fillers and binders are thus often treated as one group of pharmaceutical excipients, e.g., fillers/binders. Tablet/capsule fillers/binders are one of the most essential elements in the pharmaceutical composition of a tablet or capsule. Because they promote cohesiveness, the fillers/binders, are sometimes also referred to as adhesives, help the other ingredients in a tablet or capsule to mix. A polymeric stabilizing and matrix-forming component used as a component in a solid dispersion also has properties and functionality as a binder. Tablet/capsule fillers/binders are used to turn powder to granules; this is achieved through the process of granulation. During granulation, powder substances are accumulated to form larger particles called granules.

Commonly used fillers/binders are sugars/sugar alcohols, natural binders, synthetic/semisynthetic binders and combinations thereof, as summarized below:

| Sugars/Sugar Alcohols | Natural Binders | Synthetic/Semisynthetic Polymer |
|---|---|---|
| Sucrose | Acacia | Microcrystalline cellulose |
| Glucose (solid or liquid) | Tragacanth | Methyl- and/or Ethyl Cellulose |
| Mannitol | Gelatin | Hydroxy Propyl Methyl Cellulose (HPMC) |
| Erythritol | Starch Paste | Hydroxy Propyl Cellulose |
| Lactose | Pregelatinized Starch | Sodium Carboxy Methyl Cellulose |
| Isomalt | Alginic Acid | Polyvinyl Pyrrolidone (PVP) |
| Sorbitol | Cellulose | Polyethylene Glycol (PEG) |
| Xylitol | | Polyvinyl Alcohols |
| | | Polymethacrylates |

One will appreciate that the above listing is exemplary only and additional fillers/binders may include composites, such as silicified microcrystalline cellulose; starch and lactose (e.g., Starlac); mannitol and croscarmellose sodium; and microcrystalline cellulose and sodium carboxymethylcellulose (e.g., Avicel). One also will appreciate that polymethacrylates are available under known trade names, such as Eudragit® and Kollicoat®, with examples as follows: poly (butyl methacrylate, (2-dimethylaminoethyl) methacrylate, methyl methacrylate) 1:2:1 [CAS No. 24938-16-7] (e.g., Eudragit E 100, Eudragit E 12.5, and Eudragit E PO); poly(ethyl acrylate, methyl methacrylate) 2:1 [CAS No. 9010-88-2] (e.g., Eudragit NE 30 D, Eudragit NE 40 D, and Eudragit NM 30 D); poly(methacrylic acid, methyl methacrylate) 1:1 [CAS No. 25806-15-1] (e.g., Eudragit L 100, Eudragit L 12.5, and Eudragit L 12.5 P); poly(methacrylic acid, ethyl acrylate) 1:1 [CAS No. 25212-88-8] (e.g., Eudragit L 30 D-55 and Eudragit L 100-55); poly(methacrylic acid, methyl methacrylate) 1:2 [CAS No. 25086-15-1] (e.g., Eudragit S 100, Eudragit S 12.5, and Eudragit S 12.5 P); poly(methyl acrylate, methyl methacrylate, methacrylic acid) 7:3:1 [CAS No. 26936-24-3] (e.g., Eudragit FS 30D); poly(ethyl acrylate, methyl methacrylate, trimethylammonioethyl methacrylate chloride) 1:2:0.2 [CAS No. 33434-24-1] (e.g., Eudragit RL 100, Eudragit RL PO, Eudragit RL 30 D, and Eudragit RL 12.5); poly(ethyl acrylate, methyl methacrylate, trimethylammonioethyl methacrylate chloride) 1:2:0.1 [CAS No. 33434-24-1] (e.g., Eudragit RS 100, Eudragit RS PO, Eudragit RS 30 D, and Eudragit RS 12.5). Further, one will appreciate that additional fillers/binders may include an inorganic material, such as calcium phosphate, calcium sulfate and the like.

A suitable amount of a filler/binder ranges from about 20% to about 90% by weight, about 30% to about 80% by weight, about 40% to about 70% by weight, and about 50% to about 60% by weight.

Glidants

Glidants may be used to promote powder flow by reducing interparticle friction and cohesion. A glidant may be used in combination with a lubricant as they have small ability to reduce die wall friction. A glidant may be selected from the group consisting of anhydrous colloidal silica, calcium phosphate tribasic, powdered cellulose, hydrophobic colloidal silica, magnesium oxide, magnesium silicate, magnesium trisilicate, silicon dioxide, talc, and a combination thereof. A suitable amount of a glidant ranges from about 0.5% to about 5% by weight, about 1% to about 4% by weight and about 2% to about 3% by weight.

Lubricants

A lubricant may prevent the clumping of an active ingredient and prevent the sticking of materials to machines in any of the manufacturing steps of the whole manufacturing process. A lubricant may be selected from the group consisting of calcium stearate, glycerin monostearate, glyceryl behenate, glyceryl palmitostearate, hydrogenated castor oil, hydrogenated vegetable oil type I, light mineral oil, magnesium lauryl sulfate, magnesium stearate, medium-chain triglyceride, mineral oil, myristic acid, palmitic acid, poloxamer, polyethylene glycol, sodium benzoate, sodium chloride, sodium lauryl sulfate, sodium stearyl fumarate, stearic acid, talc, zinc stearate, and a combination thereof. A suitable amount of lubricant ranges from about 0.5% to about 5% by weight, about 1% to about 4% by weight and about 2% to about 3% by weight in each of manufacturing step where it is being used.

Antioxidants

An antioxidant may be used to suppress and/or prevent oxidation of ingredients of compositions, such as nilotinib. An antioxidant may be selected from the group consisting of α-tocopherol, ascorbyl palmitate, butylated hydroxyanisole, butylated hydroxytoluene, ethyl oleate, methionine, propyl gallate, sodium ascorbate, and a combination thereof.

Solubilizers

A solubilizers may be used to increase the solubility of a substance, such as an active pharmaceutical ingredient. A solubilizer may be selected from the group consisting of a d-α-tocopherol acid polyethylene glycol 1000 succinate, sodium dodecyl sulphate, a PEG-40 hydrogenated castor oil, a PEG-35 castor oil, a PEG-40 stearate, a hard fat, a polyoxylglyceride, a PEG-8 caprylic/capric glyceride, a poloxamer, and a combination thereof.

Disintegrants

A disintegrant is an excipient that is incorporated into the pharmaceutical composition of tablets or capsules to promote their disintegration when they come into contact with liquid or fluid matter. Several types of disintegrant may be distinguished according to their mode of action: (a) those that enhance the action of capillary forces that promote the absorption of water (by wicking) (b) those that swell on contact with water and (c) those that release gases leading directly to disintegration of the tablet, so-called effervescent tablets. The general purpose of incorporating one or more disintegrants in the product pharmaceutical composition is to increase the surface area of the product and soften the binding matter that holds together the solid particles that make up the product. The net effect is that a tablet or capsule when exposed to aqueous media disintegrates first into granules, and then into fine particles.

The growing demand for faster and more rapid disintegrating pharmaceutical compositions has stimulated the development of superdisintegrants, which may have a greater effectiveness even at a low concentration, and which may be effective as an intragranular component. Most superdisintegrants are hygroscopic and readily absorb moisture, which can have varying effects on the formulation. Absorption and swelling during storage may negatively impact the stability of the pharmaceutical composition. However, in cases where the active ingredient is moisture-sensitive, the superdisintegrant's ability to act as an internal desiccant can be advantageous.

A suitable disintegrant, such as croscarmellose sodium, crospovidone, and sodium starch glycolate, or a combination thereof may be used. A suitable amount of a disintegrant ranges from about 4% to about 16% by weight, about 6% to about 15% by weight, about 8% to about 14% by weight, about 10% to about 13% by weight, and about 11% to about 12% by weight.

Coatings

A coating material may be selected from the group consisting of carnauba wax, cellulose acetate, cellulose acetate phthalate (CAP), ceresin, cetyl alcohol, chitosan, ethylcellulose, fructose, gelatin, glycerin, glyceryl behenate, glyceryl palmitostearate, hydroxyethyl cellulose, hydroxyethylmethyl cellulose, hydroxypropyl cellulose, hypromellose, hypromellose phthalate, isomalt, latex particles, liquid glucose, macrogol 400, maltitol, maltodextrin, methylcellulose, microcrystalline wax, paraffin, poloxamer, polydextrose, polyethylene glycol, polyethylene oxide, poly-DL-(lactic acid), polyvinyl acetate phthalate, polyvinyl alcohol, povidone, shellac, shellac with stearic acid, surface color agents, titanium oxide, tributyl citrate, triethyl citrate, vanillin, white wax, xylitol, yellow wax, zein, and a combination thereof. Certain coating agents marked under the trade-name OPADRY® may be used. One grade of OPADRY® comprises hypromellose, macrogol 400, and Polysorbate 80. Any suitable coating method, like spraying may be used. A color may be added to improve the appearance of a tablet or capsule. Color consistency may be important as it allows easy identification of a medication. Some coatings are therefore colored using OPADRY® Blue or OPADRY® White, wherein titanium dioxide is the white color agent. A suitable amount of coating ranges from about 0.5% to about 3% by weight, about 1% to about 2% by weight and about 1.8% to about 1.9% by weight.

Capsules

A capsule refers to a dosage form or drug delivery system that encloses a pharmaceutical composition within a gelatin or other suitable shell, such as HPMC. These shells can be either hard or soft, and they are designed to contain the pharmaceutical composition and are used to administer medications orally.

Treatment of Proliferative Disorders

In another aspect, a composition disclosed herein may be used in therapy.

In another embodiment, a composition disclosed herein may be used in the treatment of a proliferative disorder. Typically, said proliferative disorder is selected from tumors and cancers, including, but not limited to, neurofibromatosis, tuberous sclerosis, hemangiomas and lymphangiogenesis, cervical, anal and oral cancers, eye or ocular cancer, stomach cancer, colon cancer, bladder cancer, rectal cancer, liver cancer, pancreas cancer, lung cancer, breast cancer, cervix uteri cancer, corpus uteri cancer, ovary cancer, prostate cancer, testis cancer, renal cancer, brain cancer, cancer of the central nervous system, head and neck cancer, throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, multiple myeloma; cardiac hypertrophy, age-related macular degeneration and diabetic retinopathy.

More specifically, the compositions disclosed herein may be used for treatment of: (1) adult patients with newly diagnosed Philadelphia chromosome positive chronic myeloid leukemia (Ph+CML) in chronic phase or (2) adult patients with chronic phase (CP) and accelerated phase (AP) Ph+CML resistant to or intolerant to prior therapy that included imatinib.

The composition of the present disclosure may be conveniently administered in unit dosage form; for example containing from about 5 mg to about 200 mg of nilotinib, including all values in between, such as, for example, 10 mg, 15 mg, 20 mg, 25 mg, 30 mg, 35 mg, 36 mg, 40 mg, 41 mg, 42 mg, 43 mg, 44 mg, 45 mg, 46 mg, 47 mg, 48 mg, 49 mg, 50 mg, 55 mg, 57 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg of active ingredient per unit dosage form.

General Considerations of Administering at Reduced Dosage

In addition, administration of the ASD, the composition, or the pharmaceutical composition of the present disclosure can be characterized by how the pharmacokinetic profile resulting from administration of the ASD or the pharmaceutical composition compares to the pharmacokinetic profile resulting from administration of a conventional immediate-release capsule composition, such as Tasigna® containing crystalline nilotinib monohydrochloride monohydrate.

As a point of reference, Tasigna® (nilotinib) capsules, for oral use, contain 50 mg, 150 mg, or 200 mg nilotinib base, anhydrous (equivalent to 55 mg, 166 mg, and 221 mg crystalline nilotinib monohydrochloride monohydrate, respectively) with the following inactive ingredients: colloidal silicon dioxide, crospovidone, lactose monohydrate, magnesium stearate, and poloxamer 188. The capsules contain gelatin, iron oxide (red), iron oxide (yellow), iron oxide (black), and titanium dioxide.

For instance, in some embodiments, administration of an ASD or pharmaceutical composition of the present disclosure may result in a pharmacokinetic profile that is comparable to the pharmacokinetic profile obtained by orally administering a conventional immediate-release formulation (e.g., Tasigna®), but administered at a fraction of the dosage, such as the so-called multiple capsule concept. For this comparison, administration must be done in a fasted state, since Tasigna® should only be administered in a fasted state.

The so-called multiple capsule concept is a strategy used in the pharmaceutical industry to create generic or improved versions of branded medications by utilizing smaller unit dosage forms to achieve the desired recommended therapeutic dose. This approach is particularly useful when the original product is available in higher doses that are not easily replicated in a single capsule or tablet. For instance, Tasigna® is available in 150 mg and 200 mg unit dose capsules. However, the recommended adult dose is 300 mg (consisting of two 150 mg capsules) orally twice daily for newly diagnosed Ph+CML-CP and 400 mg (consisting of two 200 mg capsules) orally twice daily for resistant or intolerant Ph+CML-CP and CML-AP.

To create a generic or improved equivalent, manufacturers could produce for example a 50 mg capsule and instruct patients to take multiple capsules to match the recommended dose. Specifically, a patient would take three 50 mg capsules to achieve the equivalent of a 150 mg unit dose and four 50 mg capsules to achieve the equivalent 200 mg unit dose. Consequently, six 50 mg unit doses capsules would be required to achieve the equivalent of a 300 mg recommended dosage and eight 50 mg unit doses capsules would be required to achieve the equivalent of a 400 mg recommended dosage.

This method offers several advantages. It can simplify the manufacturing process, as producing a single lower-dose capsule can be more straightforward and cost-effective than producing multiple higher-dose versions. Additionally, it provides flexibility in dosing, allowing for more precise adjustments to meet individual patient needs. However, it also requires careful consideration of patient compliance and convenience, as taking multiple capsules can be less convenient than a single higher-dose capsule. Overall, the multiple capsule concept is a practical solution in the development of generic medications, ensuring that patients have access to affordable and effective treatments.

For embodiments of the disclosure that can be administered at a fraction of the dosage as compared to the dosage required when administering a conventional immediate-release crystalline nilotinib composition, it can be reasoned that the inventive pharmaceutical composition is inherently safer than the corresponding conventional immediate-release capsule composition, such as Tasigna® containing crystalline nilotinib monohydrochloride monohydrate. By decreasing the required dosage while still providing an efficacious exposure to the patient, the risks of overexposure are reduced. Overexposure to nilotinib is associated with the risk of QT prolongation discussed above, which is currently the subject of a "black box warning" on the Tasigna® label. The risk of overexposure affects the entire patient population treated with nilotinib. As such, a reduced dosage inherently decreases the risk of sudden death in the patient population, since QT prolongation is reported to cause sudden cardiac death in approximately one out of every 300 Tasigna® patients.

Accordingly, certain embodiments relate to a method for treatment of: (i) adult patients greater than or equal to 1 year of age with newly diagnosed Philadelphia chromosome positive chronic myeloid leukemia (Ph+CML) in chronic phase; and (ii) adult patients with chronic phase (CP) and accelerated phase (AP) Ph+CML resistant to or intolerant to prior therapy that included imatinib; wherein the method results in a reduced risk of sudden death due to, for example, a reduction and/or elimination of QT prolongation in the patient.

Further, certain embodiments relate to a method for treatment of: (i) adult patients with newly diagnosed Philadelphia chromosome positive chronic myeloid leukemia (Ph+CML) in chronic phase; and (ii) adult patients with chronic phase (CP) and accelerated phase (AP) Ph+CML resistant to or intolerant to prior therapy that included imatinib; wherein the method results in a reduced risk of drug-drug interaction with i) strong CYP3A4 inhibitors or inducers, and ii) substrates or inhibitors of P-glycoprotein.

In addition to reducing the overall risk of overexposure, the pharmaceutical compositions of the disclosure may limit risk associated with an undesirably high Cmax. For certain risks such as QT prolongation, Cmax may in fact be the more relevant pharmacokinetic parameter. A sizable increase in Cmax, such as between fasted and fed states, may be highly undesirable and potentially unsafe. In some embodiments, the pharmaceutical compositions of the disclosure reduce or eliminate the possibility that a patient may experience an undesirably high Cmax.

With respect to the respective pharmacokinetic profiles, by "comparable," it is meant that the administration of the ASD or the pharmaceutical composition of the disclosure to the subject may provide AUC0-t (such as AUC0-24 h or AUC0-inf) or Cmax in the subject's plasma that are within the 80% to 125% bioequivalence criteria compared to administration of the immediate-release capsule formulation, such as Tasigna® containing crystalline nilotinib monohydrochloride monohydrate, to the same subject, dosed according to its labeled instructions.

As used herein, "fraction of the dosage" may mean that the dose of nilotinib in the ASD or the pharmaceutical composition of the present disclosure may be 80% less, or 75% less, or 70% less, or 65% less, or 60% less, or 55% less, or 50% less, or 45% less, or 40% less, or 35% less, or 30% less, or 25% less, or 20% less, or 15% or less, or 10% or less, as compared to the labeled dosage of the immediate-release capsule formulation, such as Tasigna® containing crystalline nilotinib monohydrochloride monohydrate.

The "fraction of the dosage" may be a pharmaceutical composition of the present disclosure in a capsule that include the entire recommended dose.

Alternatively, the "fraction of the dosage" may be a pharmaceutical composition of the present disclosure using the so-called multiple capsule concept so that a patient would take three unit dosage capsules to achieve the corresponding plasma levels of a 300 mg recommended dose of Tasigna® and four unit dosage capsules to achieve the corresponding plasma levels of a 400 mg recommended dose of Tasigna®.

Methods of Co-Administering with a Gastric Acid-Reducing Agent

Other embodiments of the present disclosure relate to the use of the nilotinib ASDs and the pharmaceutical compositions of the present disclosure with a gastric acid-reducing agent.

In one aspect, the present disclosure relates to a method of delivering nilotinib concurrently with a gastric acid-reducing agent to a patient in need thereof, comprising co-administering to the patient (a) a therapeutically effective amount of a pharmaceutical composition of the present disclosure, and (b) a therapeutically effective amount of the gastric acid-reducing agent.

In another aspect, the present disclosure relates to a method of treating a patient who has a proliferative disorder and is suffering from condition caused by the overproduction of stomach acid or exacerbated by stomach acid, the method comprising co-administering to the patient (a) a therapeutically effective amount of a pharmaceutical composition of the present disclosure, and (b) a therapeutically effective amount of a gastric acid-reducing agent.

In yet another aspect, the present disclosure relates to a method of delivering a therapeutically effective amount of nilotinib to a patient without regard to whether the patient is concurrently administered a gastric acid-reducing agent, comprising administering a therapeutically effective amount of a pharmaceutical composition of the present disclosure to the patient.

"Gastric acid-reducing agent" refers herein to any agent that acts to significantly reduce the amount of acid in a subject's stomach. Acid reduction can be due to suppression or blocking of acid secretion, or by neutralization of stomach acid. Examples of gastric acid-reducing agents include, but are not limited to, potassium-competitive acid blockers, proton pump inhibitors, histamine-2 receptor antagonists (or H2 antagonists), and antacids.

Potassium-Competitive Acid Blockers (P-CABs) are a relatively new class of medications used to reduce stomach acid. Like proton pump inhibitors (PPIs), P-CABs target acid-producing pumps in the stomach but work through a different mechanism, potentially offering some advantages.

P-CABs block the potassium-binding site on the H+/K+ ATPase enzyme (the proton pump), which is responsible for acid secretion in the stomach. This prevents the pump from exchanging potassium ions for hydrogen ions, which are necessary for producing gastric acid.

Unlike PPIs, which need to be activated in an acidic environment and may take several days to reach their full effect, P-CABs act quickly partially because they don't require acid activation.

P-CABs generally provide more sustained acid suppression over 24 hours, which can lead to better control of acid-related conditions, such as erosive esophagitis.

Other potentially advantages of P-CABs (over PPIs) comprises: (i) faster relief because P-CABs don't need to accumulate to be effective and they thus provide quicker symptom relief than PPIs; (ii) less dependence on timing of intake since PPIs need to be taken before meals to be most effective, but P-CABs can be taken at any time without significantly affecting their efficacy; and (iii) more effective for *H. pylori* treatment when used in combination therapies for treating *Helicobacter pylori* infections, which is a major cause of peptic ulcers.

Examples of P-CABs include, but are not limited to, vonoprazan, revaprazan, linaprazan, soraprazan, and tegoprazan.

Proton pump inhibitors reduce stomach acid production by blocking the hydrogen/potassium adenosine triphosphatase enzyme (i.e., the gastric proton pump) of the parietal cells, which are the epithelial cells that secrete stomach acid. Examples of proton pump inhibitors include, but are not limited to, rabeprazole, esomeprazole, lansoprazole, omeprazole, pantoprazole, and dexlansoprazole.

H2 antagonists block histamine from binding to the H2 receptors of parietal cells, thereby suppressing both the normal secretion and meal-stimulated secretion of acid by parietal cells. Examples of H2 antagonists include, but are not limited to, famotidine, cimetidine, nizatidine, and ranitidine.

Antacids contain alkaline generating ions that chemically neutralize stomach gastric acid. Examples of antacids include, but are not limited to, aluminum hydroxide, magnesium hydroxide, sodium citrate, sodium carbonate, sodium bicarbonate, calcium carbonate, and magnesium trisilicate.

The gastric acid-reducing agent may be administered in accordance with the dosing information that is known in the art for the agent, or according to a physician's instructions. A "therapeutically effective amount" of the gastric acid-reducing agent may be the amount set forth in the dosing information that is known in the art for the gastric acid-reducing agent, or according to a physician's instructions. A "standard dosage" is a dosage in accordance with a product's labeled instructions. In particular, a standard dosage is appropriate for gastric acid-reducing agents that are available over-the-counter (i.e., without a physician's prescription), such as most antacids, certain H2 antagonists, and certain proton pump inhibitors.

As used herein, a condition caused by the overproduction of stomach acid or exacerbated by stomach acid may be any condition that can be treated by reducing the amount of acid or the acidity in the subject's stomach. Examples of such a condition include, but are not limited to, dyspepsia (i.e., indigestion), gastroesophageal reflux disease, duodenal or stomach ulcers, erosive esophagitis, stress gastritis, Barrett's esophagus, and gastrinomas.

As used herein, "co-administration" (or "co-administered") refers to the administration of two or more therapeutic agents within a relevant period of time (such as one day, or 12 hours, or 8 hours, or 6 hours, for example), such that consideration must be given to whether the administration of one of the therapeutic agents may affect the absorption or efficacy of the other. Such administration may be for the treatment of two or more conditions simultaneously, such as, by way of example only, a patient requiring treatment for a proliferative disorder as described herein with nilotinib as a therapeutic agent, while also being treated for another condition, such as acid reflux or ulcers, with a second therapeutic agent such as a gastric acid-reducing agent (e.g., a proton pump inhibitor). Since both therapeutic agents are dosed at least once daily, the two therapeutic agents are "co-administered," and consideration must be given to whether the administration of one of the therapeutic agents may affect the absorption or efficacy of the other.

Embodiments of the disclosure relate to administering a gastric acid-reducing agent shortly before, concurrently with, or shortly after the dasatinib ASDs or pharmaceutical compositions of the disclosure. The term "shortly before" as used herein may mean that a gastric acid-reducing agent was administered to the subject 10 hours or less, or 8 hours or less, or 6 hours or less, or 5 hours or less, or 4 hours or less, or 3 hours or less, or 2 hours or less, or 1 hour or less, or 45 minutes or less, or 30 minutes or less, or 15 minutes or less, prior to the administration of the pharmaceutical composition of the disclosure. The term "concurrently" or "concomitantly" as used herein may mean that a gastric acid-reducing agent was administered to the subject within 30 minutes or less, or within 20 minutes or less, or within 15 minutes or less, or within 10 minutes or less, or within 5 minutes or less, or within 4 minutes or less, or within 3 minutes or less, or within 2 minutes or less, or within 1 minute or less, or simultaneously, of the administration of the pharmaceutical composition. The term "shortly after" as used herein means that a gastric acid-reducing agent was administered to the subject 6 hours or less, or 5 hours or less, or 4 hours or less, or 3 hours or less, or 2 hours or less, or 1 hour or less, or 45 minutes or less, or 30 minutes or less, or 15 minutes or less, after the administration of the pharmaceutical composition.

In the context of the present disclosure, the phrase "can be co-administered" means that the two (or more) therapeutic agents of interest can be co-administered without a detrimental reduction in the exposure of nilotinib. "Without a detrimental reduction" indicates that the realized exposure would be comparable to the exposure realized when the gastric acid-reducing agent is not co-administered. Any difference in the realized exposure would be insubstantial and/or therapeutically inconsequential. In contrast, when a detrimental reduction in exposure would be realized, then co-administration should be avoided. A "detrimental reduction" means a substantial and material reduction in the realized exposure. By way of example, if the realized exposure would be less than or equal to a level recognized as a sub-therapeutic exposure, then the co-administration would result in a detrimental reduction in exposure.

Pharmaceutical Composition Having Improved Variability

The pharmaceutical compositions of the present disclosure may, in some embodiments, provide a less variable in vivo pharmacokinetic performance compared to a reference listed drug, such as Tasigna®.

As used herein, the phrase "improved variability composition" refers to a composition of the present disclosure that exhibits a lower coefficient of variation with respect to one or more pharmacokinetic parameters when administered to an appropriate set of healthy human subjects, as compared to the coefficient of variation observed for a conventional immediate-release crystalline formulation of nilotinib (e.g., Tasigna®) when administered under similar conditions.

In some embodiments, the improved variability composition provides a coefficient of variation with respect to at least one pharmacokinetic parameter that is 30% lower, 25% lower, 20% lower, 15% lower, 10% lower, or 5% lower than the coefficient of variation observed for the standard commercial, immediate-release crystalline composition of nilotinib (e.g., Tasigna®) when administered under similar conditions. The pharmacokinetic parameter can be any of Cmax, $AUC_{0\text{-}last}$ and $AUC_{0\text{-}inf}$. In some embodiments, the improved variability composition provides an improvement with respect to Cmax and at least one of $AUC_{0\text{-}last}$ and $AUC_{0\text{-}inf}$. In other embodiments, the improved variability composition provides an improvement with respect to all of Cmax, AUClast and AUC0-inf.

In particular, it has been observed that compositions disclosed herein can provide a lower coefficient of variation for pharmacokinetic parameters when administered to human subjects (e.g., healthy human subjects) in a fasted state.

These results showed that nilotinib ASD according to the present disclosure can be used to increase nilotinib exposure in the fasted state, potentially facilitating a lower delivered dose and improved food effect profile compared to Tasigna® (crystalline nilotinib monohydrochloride monohydrate).

An aspect of the present disclosure is to provide a pharmaceutical composition that is bioequivalent, including size limitations, to the corresponding RLD, such as Tasigna® (crystalline nilotinib monohydrochloride monohydrate).

Bioequivalence of the pharmaceutical compositions of the present disclosure is established by (a) 90% Confidence Interval for the ratio (generic drug vs reference listed drug) of mean AUC(0-t), e.g., AUC(0-24 h), which is between 80% and 125%; (b) 90% Confidence Interval for the ratio (generic drug vs reference listed drug) of mean AUC(0-∞), which is between 80% and 125%; or (c) a 90% Confidence Interval for the ratio (generic drug vs reference listed drug) of mean Cmax, which is between 80% and 125%; or a combination of any features a-c above. In one aspect, the mean may be a least-squares geometric mean. In another aspect, the mean may be a log-transformed least-squares geometric mean.

Alternatively, bioequivalence of the pharmaceutical compositions of the present disclosure is established by: (a) a 90% Confidence Interval for the ratio (generic drug vs reference listed drug) of AUC(0-∞) is between 80% and 125%, and optionally without excluding any subjects with AUC(0-∞)<5% of the reference listed drug; (b) a 90% Confidence Interval the ratio (generic drug vs reference listed drug) for Cmax, which is between 80% and 125%; and without excluding any subjects with AUC(0-t), e.g., AUC (0-24 h); and (c) a 90% Confidence Interval the ratio (generic drug vs reference listed drug) of Cmax, which is between 80% and 125%; or a combination of any features a-c above.

Methods of Administering at Reduced Dosage

In addition, administration of a pharmaceutical composition, comprising an ASD disclosed herein may be characterized by how the pharmacokinetic profile resulting from administration of a pharmaceutical composition, comprising an ASD, compares to the pharmacokinetic profile resulting from administration of a conventional nilotinib composition.

For instance, in some embodiments, administration of a pharmaceutical composition, containing an ASD, of the present disclosure may result in a pharmacokinetic profile that is comparable to the pharmacokinetic profile obtained by orally administering a conventional nilotinib formulation, but administered at a fraction of the dosage (e.g., from about 0.20 to about 0.80). For this comparison, administration must be done in a fasted state, since Tasigna® should only be administered in a fasted state.

For embodiments of the disclosure that can be administered at a fraction (e.g., from about 0.20 to about 0.80, e.g., about 0.40 to about 0.50) of the dosage as compared to the dosage required when administering a conventional nilotinib composition, it can be reasoned that the inventive formulation is inherently safer than the corresponding conventional nilotinib composition. By decreasing the required dosage while still providing an efficacious exposure to the patient, the risks of overexposure are reduced.

By way of example only, a pharmaceutical composition of the present disclosure containing approximately 100 mg nilotinib free base may provide a pharmacokinetic profile that is comparable to the pharmacokinetic profile obtained by orally administering a crystalline nilotinib formulation labeled to contain 200 mg of nilotinib (such as 200 mg Tasigna® Capsule). In this example, the dose of nilotinib in the inventive pharmaceutical composition is 80% less than the dosage of the crystalline nilotinib formulation.

In some embodiments, the dose of nilotinib in a pharmaceutical composition, containing an ASD, of the present disclosure is 80% less, or 75% less, or 70% less, or 65% less, or 60% less, or 55% less, or 50% less, or 40% or less, as compared to the labeled dosage of the crystalline nilotinib monohydrate formulation. In one aspect, the dose of nilotinib in a pharmaceutical composition disclosed herein has a reduced dosage amount (e.g., from about 0.20 to about 0.80) compared to the labeled dosage of the crystalline nilotinib formulation. For instance, a pharmaceutical composition disclosed herein may include nilotinib in an amount of about 20 mg to about 80 mg, and all values in between including 21 mg, 22 mg, 23 mg, 24 mg, 25 mg, 26 mg, 27 mg, 28 mg, 29 mg 30 mg, 35 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 60 mg, 65 mg, 70 mg, and 75 mg.

In one aspect, a pharmaceutical composition disclosed herein may include nilotinib in amount of about 24 mg, which exhibits bioequivalence to Tasigna® (50 mg).

In another aspect, a pharmaceutical composition disclosed herein may include nilotinib in amount of about 48 mg, which exhibits bioequivalence to Tasigna® (100 mg).

In another aspect, a pharmaceutical composition disclosed herein may include nilotinib in amount of about 72 mg, which exhibits bioequivalence to Tasigna® (150 mg).

In another aspect, a pharmaceutical composition disclosed herein may include nilotinib in amount of about 96 mg, which exhibits bioequivalence to Tasigna® (200 mg).

In yet another aspect, a pharmaceutical composition disclosed herein comprising an amorphous solid dispersion of nilotinib of about 96 mg of nilotinib (2×48 mg unit doses) which exhibits bioequivalence to Tasigna® 200 mg Capsules containing nilotinib monohydrochloride monohydrate.

A further aspect relates to a pharmaceutical composition disclosed herein comprising an amorphous solid dispersion of nilotinib of about 144 mg of nilotinib (3×48 mg unit doses) that is bioequivalent to a recommended dose two Tasigna® 150 mg Capsules (300 mg dose) containing nilotinib monohydrochloride monohydrate.

Yet a further aspect relates to a pharmaceutical composition comprising an amorphous solid dispersion of nilotinib of about 192 mg of nilotinib (4×48 mg unit doses) that is bioequivalent to a recommended dose two Tasigna® 200 mg Capsules (400 mg dose) Capsules containing nilotinib monohydrochloride monohydrate.

The pharmaceutical compositions disclosed herein may be used for treatment of: (1) adult patients greater than or equal to 1 year of age with newly diagnosed Philadelphia chromosome positive chronic myeloid leukemia (Ph+CML) in chronic phase; and (2) adult patients with chronic phase (CP) and accelerated phase (AP) Ph+CML resistant to or intolerant to prior therapy that included imatinib; by administering to a patient in need thereof a pharmaceutical composition disclosed herein comprising a therapeutically effective amount of nilotinib.

In another aspect, the pharmaceutical compositions disclosed herein may be used for treatment of: (1) adult patients greater than or equal to 1 year of age with newly diagnosed Philadelphia chromosome positive chronic myeloid leukemia (Ph+CML) in chronic phase; and (2) adult patients with chronic phase (CP) and accelerated phase (AP) Ph+CML resistant to or intolerant to prior therapy that included imatinib; by administering to a patient in need thereof a pharmaceutical composition disclosed herein comprising a therapeutically effective amount of nilotinib.

In one aspect, a therapeutically effective amount of nilotinib includes at least one dose amount selected from the group consisting of 24 mg nilotinib, 48 mg nilotinib, 72 mg nilotinib, 96 mg nilotinib, 144 mg nilotinib, and 192 mg nilotinib, where the nilotinib amount is based on nilotinib free base.

Packaging

Pharmaceutical compositions disclosed herein may be packaged in a suitable container that comprises at least one capsule and optionally a desiccant. The packaging may further comprise written materials identifying dosing and administration with respect to the methods of treatment disclosed herein. The written material will instruct the patient to swallow the capsules whole with water. The written material will not encourage the patient to disperse the capsule contents in a fruit preparation, such as applesauce.

EXAMPLES

The following examples illustrate aspects disclosed herein and are not intended to limit the appended claims.

Example 1

Nilotinib ASD was prepared with copovidone as the at least one polymeric stabilizing and matrix-forming component (e.g., nilotinib (about 25% w/w) and copovidone (about 75% w/w)).

Capsules were prepared in weight ratios (such as milligram or gram) shown below in Tables 1, 2 and 3. The ingredients were dry blended by diffusive mixing (Turbula® blending) to homogeneous blends which were manually filled into hard-shell HPMC capsules of size 1.

TABLE 1

Compositional makeup of capsules of Example 1
(no weak acid added, sample E1T1(or E1C1))

| Ingredient | Supplier | mg/unit | % of unit |
|---|---|---|---|
| Nilotinib ASD ≈25% w/w drug load, milled | Xspray Pharma | 120 | 50.0 |
| Eudragit L100-55 | Evonik | 30 | 12.5 |
| Mannitol 200SD | Roquette | 87 | 36.3 |
| Silicon dioxide | Grace | 2 | 0.8 |
| Sodium stearyl fumarate | JRS Pharma | 1 | 0.4 |
| Final blend | Total | 240 mg | 100% |

TABLE 2

Compositional makeup of capsules of Example 1
(citric acid added, sample E1T2 (or E1C2))

| Ingredient | Supplier | mg/unit | % of unit |
|---|---|---|---|
| Nilotinib ASD ≈25% w/w drug load, milled | Xspray Pharma | 120 | 49.8 |
| Eudragit L100-55 | Evonik | 30 | 12.4 |
| Citric acid, anhydrous, crystalline powder | Sigma-Aldrich | 40 | 16.6 |
| Mannitol 200SD | Roquette | 49 | 20.3 |
| Silicon dioxide | Grace | 1 | 0.4 |
| Sodium stearyl fumarate | JRS Pharma | 1 | 0.4 |
| Final blend | Total | 241 mg | 100% |

TABLE 3

Compositional makeup of capsules of Example 1
(ascorbic acid added, sample E1T3 (or E1C3))

| Ingredient | Supplier | mg/unit | % of unit |
|---|---|---|---|
| Nilotinib ASD ≈25% w/w drug load, milled | Xspray Pharma | 120 | 50.0 |
| Eudragit L100-55 | Evonik | 30 | 12.5 |
| Ascorbic acid, crystalline powder | Sigma-Aldrich | 40 | 16.7 |
| Mannitol 200SD | Roquette | 48 | 20.0 |
| Silicon dioxide | Grace | 1 | 0.4 |
| Sodium stearyl fumarate | JRS Pharma | 1 | 0.4 |
| Final blend | Total | 240 mg | 100% |

Samples of each of E1T1, E1T2, and E1T3 were stored at 40° C./60% relative humidity for about 12 weeks and the Nilotinib Impurity A content observed was 3.1 ppm (E1T1), 91.3 ppm (E1T2), and 4.6 ppm (E1T3). The composition including citric acid (E1T2), showed a substantial amount of Nilotinib Impurity A relative to the composition with no acid (E1T1) and the composition with ascorbic acid (E1T3).

Example 2

The dissolution profile of the compositional makeups of Example 1 (viz., samples E1T1, E1T2, and E1T3) filled into hard-shell HPMC capsules were recorded using USP Dissolution Test 2 (0.01 M HCl, 500 mL, 37.0±0.5° C., 75 rpm) sampling at 10, 20, 30, 46, 60, and 76 minutes with a 2-mL sample volume that were filtered through a pre-wet 45 μm PTFE inline filter and analyzed by HPLC. FIG. 1 of U.S. Provisional Patent Application No. 63/596,990 shows the average dissolution results for six capsules for each sample prepared according to Example 1 reporting % nilotinib (by HPLC) dissolved vs. time. The results showed that nilotinib-containing capsules with acid (e.g., ascorbic acid/citric acid) exhibited a greater degree of dissolution compared to nilotinib-containing capsules with no acid. And this data, along with pharmacokinetic results presented herein, shows that pharmaceutical compositions disclosed herein are immediate release compositions.

Example 3

Nilotinib ASD was prepared with copovidone as the at least one polymeric stabilizing and matrix-forming component.

Powder blends were prepared in weight ratios (such as milligram or gram) shown below in Tables 4 and 5. The ingredients were dry blended by diffusive mixing (Turbula® blending) to homogeneous blends. Approximately one gram of each powder blend and one gram of neat Nilotinib ASD was separately dispensed into 20-mL glass vials.

TABLE 4

Sample E3T4, powder blend with Nilotinib ASD and citric acid.

| Ingredient | Supplier | mg/unit | % of unit |
|---|---|---|---|
| Nilotinib ASD 25% drug load, milled | Xspray Pharma | 120 | 57.1 |
| Eudragit L100-55 | Evonik | 60 | 28.6 |

TABLE 4-continued

Sample E3T4, powder blend with Nilotinib ASD and citric acid.

| Ingredient | Supplier | mg/unit | % of unit |
|---|---|---|---|
| Citric acid, anhydrous, crystalline powder | Sigma-Aldrich | 30 | 14.3 |
| Final blend | Total | 210 mg | 100% |

TABLE 5

Sample E3T5, powder blend with Nilotinib ASD and ascorbic acid.

| Ingredient | Supplier | mg/unit | % of unit |
|---|---|---|---|
| Nilotinib ASD 25% drug load, milled | Xspray Pharma | 120 | 57.1 |
| Eudragit L100-55 | Evonik | 60 | 28.6 |
| Ascorbic acid, crystalline powder | Sigma-Aldrich | 30 | 14.3 |
| Final blend | Total | 210 mg | 100% |

The storage stability of the powder blends and Nilotinib ASD were tested at 40° C. and 75% relative humidity in their closed containers. After five weeks storage the samples were analyzed for Nilotinib impurity A by LC/MS.

The results in Table 6 show that the powder blend with ascorbic acid, sample E3T5, had a significantly lower amount of Nilotinib impurity A compared to the powder blend with citric acid, sample E3T4.

TABLE 6

The levels of Nilotinib impurity A in powder blends of: (i) E3T4; (iii) E3T5, and (iii) Nilotinib ASD (no acid) after 5 weeks storage at 40° C. and 75% relative humidity.

| | | Nilotinib impurity A (ppm) | | |
|---|---|---|---|---|
| Sample | Description | Analysis A | Analysis B | Average |
| E3T4 | Nilotinib ASD* with L100-55 and citric acid | 5.11 | 5.32 | 5.22 |
| E3T5 | Nilotinib ASD* with L100-55 and ascorbic acid | 1.43 | 1.32 | 1.38 |
| | Nilotinib ASD* | 1.85 | 1.84 | 1.85 |

*Analyzed Nilotinib ASD (with about 25% w/w nilotinib and about 75% w/w copovidone) was from the same batch used for each of samples E3T4 and E3T5.

Example 4

Nilotinib ASD was prepared with copovidone as the at least one polymeric stabilizing and matrix-forming component (e.g., nilotinib (about 25% w/w) and copovidone (about 75% w/w)). Particulate Nilotinib ASD, as described herein, was used.

Capsules were prepared in weight ratios (such as milligram or gram) shown below in Table 7 (i.e., Comp. Nos. 6-22). The ingredients were dry blended by diffusive mixing to homogeneous blends which were either manually filled or machine filled (e.g., MG2 Suprema) into hard-shell HPMC capsules of size 1.

TABLE 7

Description of HPMC Capsules for Composition Nos. 6-22

| Ingredient | Comp. No. | | | | | | | | | |
|---|---|---|---|---|---|---|---|---|---|---|
| | 6 | 7 | 8 | 9 | 10 | 11 | 12 | 13 | 14 | 15 |
| | Amount (mg) | | | | | | | | | |
| Nilo (ASD)(1) | 30.00 | 30.00 | 30.00 | 30.00 | 30.00 | 35.00 | 35.00 | 35.00 | 30.00 | 30.00 |
| AA(2) | 30.00 | 20.00 | 40 | 50.00 | 30.00 | 50.00 | 52.00 | 52.00 | 43.80 | 25.00 |
| CA(3) | — | 20.00 | — | 10.00 | 10.00 | — | — | — | — | 25.00 |
| B/F(4) | 60.00 | 30.00 | 30.00 | 30.00 | 30.00 | 25.00 | 18.00 | 9.00 | 30.00 | 30.00 |
| B/F(5) | — | 48.00 | 48.00 | 28.00 | 48.00 | 62.00 | 67.00 | 76.00 | 43.80 | 37.00 |
| Glidant(6) | — | 1.00 | 1.00 | 1.00 | 1.00 | 1.50 | 1.50 | 1.50 | 1.20 | 2.00 |
| Lubricant(7) | — | 1.00 | 1.00 | 1.00 | 1.00 | 1.50 | 1.50 | 1.50 | 1.20 | 1.00 |
| Total | 210 | 240 | 240 | 240 | 240 | 280 | 280 | 280 | 240 | 240 |
| AA/Nilo | 1.0 | 0.67 | 1.33 | 1.67 | 1.00 | 1.43 | 1.49 | 1.49 | 1.46 | 0.83 |

| Ingredient | Comp. No. | | | | | | |
|---|---|---|---|---|---|---|---|
| | 16 | 17 | 18 | 19 | 20 | 21 | 22 |
| | Amount (mg) | | | | | | |
| Nilo (ASD)(1) | 30.00 | 30.00 | 35.00 | 40.00 | 45.00 | 41.00 | 48.00 |
| AA(2) | 50.00 | 43.80 | 51.10 | 58.40 | 65.70 | 59.86 | 70.08 |
| CA(3) | — | — | — | — | — | — | — |
| B/F(4) | 30.00 | 30.00 | 35.00 | 40.00 | 45.00 | 41.00 | 48.00 |
| B/F(5) | 37.00 | 43.80 | 51.10 | 56.40 | 65.70 | 59.86 | 70.08 |

TABLE 7-continued

Description of HPMC Capsules for Composition Nos. 6-22

| | | | | | | | |
|---|---|---|---|---|---|---|---|
| Glidant(6) | 2.00 | 1.20 | 1.40 | 1.60 | 1.80 | 1.64 | 1.92 |
| Lubricant(7) | 1.00 | 1.20 | 1.40 | 1.60 | 1.80 | 1.64 | 1.92 |
| Total | 240 | 240 | 280 | 320 | 360 | 328 | 384 |
| AA/Nilo | 1.67 | 1.46 | 1.46 | 1.46 | 1.46 | 1.46 | 1.46 |

Notes:
(1)Nilo-ASD has a 25% drug load which means that e.g. 30 mg Nilotinib is provided as 120 mg Nilotinib-ASD
(2)AA (ascorbic acid).
(3)CA (citric acid).
(4)B/F (binder/filler, e.g., synthetic/semisynthetic polymer, such as Eudragit L. 100-55).
(5)B/F (binder/filler, e.g., sugar, such as mannitol).
(6)Glidant (e.g., silicon dioxide).
(7)Lubricant (e.g., sodium stearyl fumarate).

Example 5

Nilotinib ASD was prepared with copovidone as the at least one polymeric stabilizing and matrix-forming component (e.g., nilotinib (about 25% w/w) and copovidone (about 75% w/w)). Particulate Nilotinib ASD, as described herein, was used.

Capsules were prepared in weight ratios (such as milligram or gram) shown below in Table 8 (i.e., Composition Nos. 23-31 with varying amounts of nilotinib, e.g., 30 mg (No. 23), 35 mg (No. 24), 40 mg (No. 25), 41 mg (No. 26), 45 mg (No. 27), 46 mg (No. 28), 47 mg (No. 29), 48 mg (No. 30), and 51 mg (No. 31)). The ingredients were dry blended by diffusive mixing (Turbula® blending) to homogeneous blends which were manually filled into hard-shell HPMC capsules of size 1.

TABLE 8

Description of HPMC Capsules for Composition Nos. 23-31

| | Comp. No. | | | | | | | | |
|---|---|---|---|---|---|---|---|---|---|
| | 23 | 24 | 25 | 26 | 27 | 28 | 29 | 30 | 31 |
| | | | | | Nilotinib (mg) | | | | |
| | 30 | 35 | 40 | 41 | 45 | 46 | 47 | 48 | 51 |
| Ingredients | | | | | Amount (mg) | | | | |
| Nilo-ASD(1) | 120.00 | 140.00 | 160.00 | 164.00 | 180.00 | 184.00 | 188.00 | 192.00 | 204.00 |
| AA(2) | 43.80 | 51.10 | 58.40 | 59.86 | 65.70 | 67.16 | 68.62 | 70.08 | 74.46 |
| Mannitol 200SD | 43.80 | 51.10 | 58.40 | 59.86 | 65.70 | 67.16 | 68.62 | 70.08 | 74.46 |
| Eudragit L100-55 | 30.00 | 35.00 | 40.00 | 41.00 | 45.00 | 46.00 | 47.00 | 48.00 | 51.00 |
| SiO2(3) | 1.20 | 1.40 | 1.60 | 1.64 | 1.80 | 1.84 | 1.88 | 1.92 | 2.04 |
| Sodium stearyl fumarate | 1.20 | 1.40 | 1.60 | 1.64 | 1.80 | 1.84 | 1.88 | 1.92 | 2.04 |
| Total | 240 | 280 | 320 | 328 | 360 | 368 | 376 | 384 | 408 |

Notes:
(1)For Comp. Nos. 23-31, Nilo-ASD has about 25% w/w of nilotinib, which means that 120 mg of Nilo-ASD includes about 30 mg and about 90 mg copovidone.
(2)Ascorbic acid.
(3)Silicon dioxide.

Example 6

Dose finding clinical trial. An open-label, single-center, randomized, three-treatment, three-period, three-sequence, single dose, crossover study to evaluate the comparative bioavailability of two test products (T1 and T2), T1 was a capsule formulation of 82 mg nilotinib (presented as two capsules containing 41 mg nilotinib each), while T2 was a capsule formulation of 164 mg nilotinib (presented as four capsules containing 41 mg nilotinib each). Composition No. 26 (Table 6) provides the compositional makeup of exemplified capsules comprising 41 mg nilotinib.

The two test products (i.e., T1 and T2), as a single dose, were compared with the reference product Tasigna® (nilotinib) capsules 200 mg (Novartis) in healthy, adult, male human subjects under fasted conditions.

The clinical trial was also used to evaluate the safety and tolerability of the test (T1 and T2) and reference formulations in healthy, adult, male human subjects.

A 21 day screening period preceded enrollment. In each study period, twenty-seven (27) blood samples were collected to assess the pharmacokinetic profile of nilotinib. Pharmacokinetic parameters were calculated from the nilotinib plasma drug concentration-time profile by non-compartmental modeling using Phoenix® WinNonlin® Version 8.4. Statistical comparison of pharmacokinetic parameters to assess the bioavailability of nilotinib formulations (T1 vs R & T2 vs R) were carried out using analysis of variance method of SAS® Studio 3.6 (Basic Edition) (SAS® Institute Inc., USA). Analysis of plasma nilotinib concentrations was done by a validated LC-MS/MS method.

TABLE 9

Bioequivalence Summary of T1 (82 mg) vs R (200 mg)

| Parameter | Least square Geometric Means | | T1/R Ratio (%) | 90% Confidence Intervals | | Power (%) | Intra Subject CV (%) | Inter Subject CV Test (%) |
|---|---|---|---|---|---|---|---|---|
| | T1 | R | | Lower (%) | Upper (%) | | | |
| Cmax (ng/ml) | 495.21 | 494.32 | 100.18 | 86.69 | 115.77 | 81.64 | 31.8 | 26.6 |
| AUCt (hr*ng/ml) | 9248.37 | 11208.15 | 82.51 | 72.20 | 94.30 | 86.72 | 29.3 | 40.1 |
| AUCinf (hr*ng/ml) | 9500.93 | 11346.29 | 83.74 | 73.46 | 95.45 | 87.82 | 28.7 | 39.2 |

TABLE 10

Bioequivalence Summary of T2 (164 mg) vs R (200 mg)

| Parameter | Least square Geometric Means | | T2/R Ratio (%) | 90% Confidence Intervals | | Power (%) | Intra Subject CV (%) | Inter Subject CV Test (%) |
|---|---|---|---|---|---|---|---|---|
| | T2 | R | | Lower (%) | Upper (%) | | | |
| Cmax (ng/mL) | 827.26 | 494.32 | 167.35 | 144.82 | 193.40 | 81.64 | 31.8 | 26.6 |
| AUCt (hr*ng/ml) | 15300.48 | 11208.15 | 136.51 | 119.45 | 156.01 | 86.72 | 29.3 | 40.1 |
| AUCinf (hr*ng/ml) | 15406.75 | 11346.29 | 135.79 | 119.12 | 154.79 | 87.82 | 28.7 | 39.2 |

Based on the observed pharmacokinetic results, the pharmaceutical composition disclosed herein may be classified as an "immediate release" dosage form where the majority of nilotinib will generally be released in a relatively short period of time, e.g., less than about 2-hours, less than about 1-hour, less than about 50-minutes, etc.

Example 7

A dose of 82 mg (2×41 mg unit doses) is associated with T/R AUC and Cmax ratios that are approximately 83% and 100%, respectively.

Equivalent unit dose calculations were done using these results. Potency of the different formulations was assumed to be 100% for future studies. The results will be used in a future pivotal study.

| | LSM T | LSM R | Ratio T/R |
|---|---|---|---|
| AUCLST | 9248 | 11208 | 82.5 |
| AUCINF | 9501 | 11346 | 83.7 |
| CMAX | 495 | 494 | 100.2 | ii) A dose of 96 mg (2×48 mg unit doses) was calculated to provide AUC T/R ratios between 95 and 100%. The Cmax T/R ratio is expected to be approximately 117%.

| | LSM T1 | LSM R | Ratio T1/R |
|---|---|---|---|
| AUCLST | 10827 | 11208 | 96.6 |
| AUCINF | 11123 | 11346 | 98.0 |
| CMAX | 580 | 494 | 117.3 | iii) A dose of 90 mg (2×45 mg unit doses) was calculated to provide AUC T/R ratios at approximately 90%. The Cmax T/R ratio is expected to be approximately 110%.

| | LSM T1 | LSM R | Ratio T1/R |
|---|---|---|---|
| AUCLST | 10151 | 11208 | 90.6 |
| AUCINF | 10428 | 11346 | 91.9 |
| CMAX | 544 | 494 | 110.0 |

DISCLOSED INFORMATION

Buehler, G., *History of Bioequivalence for Critical Dose Drugs*, FDA, 2010 ("Buehler 2010").

*Guidance for Industry: Food-Effect Bioavailability and Fed Bioequivalence Studies*, U.S. Department of Health and Human Services, Food and Drug Administration, Center for Drug Evaluation and Research (CDER), December 2002 ("FDA's 2002 Guidance").

*Guidance for Industry: M7 (R1) Assessment and Control of DNA Reactive (Mutagenic) Impurities in Pharmaceuticals to Limit Potential Carcinogenic Risk*, U.S. Department of Health and Human Services, Food and Drug Administration, Center for Drug Evaluation and Research (CDER), December 2002 ("FDA's 2018 Guidance").

Puppala et al., *Trace level detection and quantification of genotoxic impurities 3-amino-4-methylbenzoate, 3-amino-4-methylbenzoic acid, and 3-(4-methyl-1H-imidazol-1-yl)-5 (trifluoromethyl) aniline in Nilotinib dihydrochloride active pharmaceutical ingredient using liquid chromatography-tandem mass spectrometry*, Sep. Sci. Plus (2022) 5:349-356 ("Puppala").

Singamsetti et al., *Forced Degradation Studies of Nilotinib Hydrochloride: Isolation, Identification, and Characterization of Impurities*, International Journal of Pharmaceutical Sciences and Drug Research 2020; 12 (5): 537-543) ("Singamsetti").

Tasigna® (nilotinib) capsules, prescribing information, as of Sep. 23, 2021.

USP 32, *General Notices and Requirements*, 2009 ("USP 32").

U.S. Patent Application Publication No. US 2015/0273070 A1, Modified release of 4-methyl-3-[[4-(3-pyridinyl)-2-pyrimidinyl]amino]-N-[5-(4-methyl-1H-imidazol-1-yl)-3-(trifluoromethyl)phenyl]benzamide solubilized using organic acids, published on Oct. 1, 2015 to Li et al. ("Li").

To the extent necessary, information disclosed herein is incorporated by reference, including, U.S. Provisional Patent Application No. 63/596,990, filed on Nov. 8, 2023.

ADDITIONAL ASPECTS

The following information includes additional aspects disclosed herein.

Aspect 1. A composition comprising: an amorphous solid dispersion (ASD) comprising nilotinib and at least one polymeric stabilizing and matrix-forming component; and at least one solid organic acid in admixture with the ASD.

As related to Aspect 1 (or any other aspect), the expression "comprising" may be replaced with the expression "consisting of," such that an alternative to Aspect 1 relates to a composition consisting of: an amorphous solid dispersion (ASD) comprising nilotinib and at least one polymeric stabilizing and matrix-forming component; and at least one solid organic acid in admixture with the ASD.

Aspect 2. The composition of Aspect 1, wherein the at least one solid organic acid comprises ascorbic acid.

Aspect 3. The composition of Aspect 1, wherein the at least one solid organic acid comprises ascorbic acid and citric acid.

Aspect 4. The composition of any one of Aspects 2-3, wherein the amount of ascorbic acid is about 0.1-10 times the amount of nilotinib (weight to weight).

Aspect 5. The composition of any one of Aspects 2-4, wherein the amount of ascorbic acid is about 0.5-5, 0.8-4, 1-3, 1.2-2.5, 1.3-2, 1.3-1.6, 1.4-1.5, or 1.4-1.7 times the amount of nilotinib (weight to weight).

Aspect 6. A composition comprising: an amorphous solid dispersion (ASD) comprising nilotinib and at least one polymeric stabilizing and matrix-forming component; and ascorbic acid in admixture with the ASD having about 0.1 to about 100 ppm of Nilotinib Impurity A.

Aspect 7. The composition of Aspect 6, wherein the amount of ascorbic acid is about 0.5-5, 0.8-4, 1-3, 1.2-2.5, 1.3-2, 1.3-1.6, 1.4-1.5, or 1.4-1.7 times the amount of nilotinib (weight to weight).

Aspect 8. A pharmaceutical composition comprising the composition of any one of Aspects 6-7 and one or more pharmaceutically acceptable excipients.

Aspect 9. A pharmaceutical composition comprising: an amorphous solid dispersion (ASD) comprising nilotinib and at least one polymeric stabilizing and matrix-forming component; at least one solid organic acid in admixture with the ASD; and one or more pharmaceutically acceptable excipients.

Aspect 10. The pharmaceutical composition of Aspect 9, wherein the at least one solid organic acid comprises ascorbic acid.

Aspect 11. The pharmaceutical composition of Aspect 9, wherein the at least one solid organic acid comprises ascorbic acid and citric acid.

Aspect 12. The pharmaceutical composition of any one of Aspects 8-11, wherein the amount of ascorbic acid is about 0.1-10 times the amount of nilotinib (weight to weight).

Aspect 13. The pharmaceutical composition of any one of Aspects 8-11, wherein the amount of ascorbic acid is about 0.5-5, 0.8-4, 1-3, 1.2-2.5, 1.3-2, 1.3-1.6, 1.4-1.5, or 1.4-1.7 times the amount of nilotinib (weight to weight).

Aspect 14. The pharmaceutical composition of any one of Aspects 8-11, wherein the amount of ascorbic acid is about 1.5 times the amount of nilotinib (weight to weight).

Aspect 15. The pharmaceutical composition of any one of Aspects 8-14, wherein the ASD comprises particulate ASD having (1) a bulk density of about 0.42 g/mL, (2) a tapped density of about 0.63 g/mL, and (3) a particle size distribution of about 72% w/w (<125 μm), about 20.8% w/w (125-250 μm), about 5.7% w/w (250-425 μm), about 0.7% w/w (425-600 μm), and about 0.8% w/w (>600 μm).

Aspect 16. A pharmaceutical composition disclosed herein comprising an amorphous solid dispersion of nilotinib of about 96 mg of nilotinib (2×48 mg unit doses) which exhibits bioequivalence to Tasigna® 200 mg Capsules containing nilotinib monohydrochloride monohydrate.

Aspect 17. A pharmaceutical composition disclosed herein comprising an amorphous solid dispersion of nilotinib of about 144 mg of nilotinib (3×48 mg unit doses) that is bioequivalent to a recommended dose two Tasigna® 150 mg Capsules (300 mg dose) containing nilotinib monohydrochloride monohydrate.

Aspect 18. A pharmaceutical composition comprising an amorphous solid dispersion of nilotinib of about 192 mg of nilotinib (4×48 mg unit doses) that is bioequivalent to a recommended dose two Tasigna® 200 mg Capsules (400 mg dose) Capsules containing nilotinib monohydrochloride monohydrate.

Aspect 19. A method for the treatment of adult patients with newly diagnosed Philadelphia chromosome positive chronic myeloid leukemia (Ph+CML) in chronic phase, comprising: administering to the patient in need thereof the pharmaceutical composition of any one of Aspects 8-17 comprising a therapeutically effective amount of nilotinib.

Aspect 20. A method for the treatment of adult patients with chronic phase (CP) and accelerated phase (AP) Ph+CML resistant to or intolerant to prior therapy that included imatinib, comprising: administering to the patient in need thereof the pharmaceutical composition of any one of Aspects 8-17 comprising a therapeutically effective amount of nilotinib.

Aspect 20. A pharmaceutical composition of any one of Aspects 8-18 for use in the treatment of adult patients with newly diagnosed Philadelphia chromosome positive chronic myeloid leukemia (Ph+CML) in chronic phase, wherein the pharmaceutical composition comprises a therapeutically effective amount of nilotinib.

Aspect 21. A pharmaceutical composition of any one of Aspects 8-18 for use in the treatment of adult patients with chronic phase (CP) and accelerated phase (AP) Ph+CML resistant to or intolerant to prior therapy that included imatinib, wherein the pharmaceutical composition comprises a therapeutically effective amount of nilotinib.

The invention claimed is:
1. A composition comprising:
   (a) a particulate amorphous solid dispersion (ASD) comprising nilotinib free base and copovidone; and
   (b) asborbic acid in admixture with the particular ASD;
      wherein the nilotinib is present in an amount of from abuot 20% w/w to about 30% w/w of the particulate ASD; and
      wherein the ascorbic acid is present in an amount of from about 0.5 to about 5 times the amount of nilotinib (weight to weight).
2. The composition of claim 1, wherein the ascorbic acid is present in an amount of from about 1 to about 3 times the amount of nilotinib (weight to weight).
3. The composition of claim 1, wherein the ascorbic acid is present in an amount of from about 1 to about 1.5 times the amount of nilotinib (weight to weight).
4. The composition of claim 1, wherein the ascorbic acid is present in an amount of about 1.3-1.6 times the amount of nilotinib (weight to weight).
5. The composition of claim 1, wherein the particulate ASD has one or more of (1) a bulk density of about 0.42 g/mL, (2) a tapped density of about 0.63 g/mL, and (3) a particle size distribution of about 72% w/w (<125 μm), about 20.8% w/w (125-250 μm), about 5.7% w/w (250-425 μm), about 0.7% w/w (425-600 μm), and about 0.8% w/w (>600 μm).
6. The composition of claim 1, wherein the composition has about 0.1 to about 100 ppm of Nilotinib Impurity A.
7. A pharmaceutical composition comprising the composition of claim 6 and one or more pharmaceutically acceptable excipients.
8. The pharmaceutical composition of claim 7, wherein the ascorbic acid is present in an amount of about 1.3-1.6 times the amount of nilotinib (weight to weight).
9. The pharmaceutical composition of claim 7, wherein the ascorbic acid is present in an amount of about 1.5 times the amount of nilotinib (weight to weight).
10. The pharmaceutical composition of claim 7, wherein the particulate ASD has one or more of (1) a bulk density of about 0.42 g/mL, (2) a tapped density of about 0.63 g/mL, and (3) a particle size distribution of about 72% w/w (<125 μm), about 20.8% w/w (125-250 μm), about 5.7% w/w (250-425 μm), about 0.7% w/w (425-600 μm), and about 0.8% w/w (>600 μm).
11. A method for the treatment of a condition in a patient, which comprises: administering to the patient in need thereof the pharmaceutical composition of claim 7 comprising a therapeutically effective amount of nilotinib;
   wherein the condition is selected from the group consisting of:
   (1) for an adult patient with newly diagnosed Philadelphia chromosome positive chronic myeloid leukemia (Ph+CML) in chronic phase; and
   (2) for adult patients with chronic phase (CP) and accelerated phase (AP) Ph+CML resistant to or intolerant to prior therapy that included imatinib.
12. The pharmaceutical composition of claim 7, wherein the one or more pharmaceutically acceptable excipients comprises a poly(methacrylic acid, ethyl acrylate).
13. The composition of claim 1, wherein the particulate ASD consists of nilotinib free base and copovidone.
14. The composition of claim 1, wherein the nilotinib is present in an amount of about 25% w/w of the particulate ASD.
15. An immediate release pharmaceutical composition comprising the composition of claim 14 and one or more pharmaceutically acceptable excipients comprising a poly(methacrylic acid, ethyl acrylate).
16. A method for the treatment of a condition in a patient, which comprises: administering to the patient in need thereof the pharmaceutical composition of claim 15 comprising a therapeutically effective amount of nilotinib;
   wherein the condition is selected from the group consisting of:
   (1) for an adult patient with newly diagnosed Philadelphia chromosome positive chronic myeloid leukemia (Ph+CML) in chronic phase; and
   (2) for adult patients with chronic phase (CP) and accelerated phase (AP) Ph+CML resistant to or intolerant to prior therapy that included imatinib.
17. The composition of claim 1, wherein the ascorbic acid is present in an abount of about 1 to about 1.5 times the amount of nilotinib (weight to weight) and an amount of Nilotinib Impurity A is less than about 6 ppm.
18. An immediate release pharmaceutical composition comprising the composition of claim 14 and one or more pharmaceutically acceptable excipients; wherein an amount of Nilotinib Impurity A is less than about 6 ppm.
19. A method for the treatment of a condition in a patient, which comprises: administering to the patient in need thereof the pharmaceutical composition of claim 18 comprising a therapeutically effective amount of nilotinib;
   wherein the condition is selected from the group consisting of:
   (1) for an adult patient with newly diagnosed Philadelphia chromosome positive chronic myeloid leukemia Ph+CML) in chronic phase; and
   (2) for adult patients with chronic phase (CP) and accelerated phase (AP) Ph+CML resistant to or intolerant to prior therapy that included imatinib.
20. The composition of claim 1 having about 1.4 ppm nilotinib impurity A after 5 weeks when stored at 40° C. and 75% humidity.

* * * * *